(12) United States Patent
McGrath et al.

(10) Patent No.: US 11,547,744 B2
(45) Date of Patent: Jan. 10, 2023

(54) NUTRITIONAL FORMULA

(71) Applicant: Building Block Nutritionals, LLC, Charlottesville, VA (US)

(72) Inventors: James McGrath, Port Charlotte, FL (US); Paul Manning, Troy, VA (US); Eugene Scavola, Charlottesville, VA (US)

(73) Assignee: Building Block Nutritionals, LLC, Charlottesville, VA (US)

(*) Notice: Subject to any disclaimer, the term of this patent is extended or adjusted under 35 U.S.C. 154(b) by 116 days.

(21) Appl. No.: 16/315,132

(22) PCT Filed: Jul. 6, 2017

(86) PCT No.: PCT/US2017/040879
§ 371 (c)(1),
(2) Date: Jan. 3, 2019

(87) PCT Pub. No.: WO2018/009647
PCT Pub. Date: Jan. 11, 2018

(65) Prior Publication Data
US 2019/0247469 A1 Aug. 15, 2019

Related U.S. Application Data

(60) Provisional application No. 62/359,033, filed on Jul. 6, 2016.

(51) Int. Cl.
*A61K 38/38* (2006.01)
*A23L 33/12* (2016.01)
(Continued)

(52) U.S. Cl.
CPC .............. *A61K 38/38* (2013.01); *A23L 33/00* (2016.08); *A23L 33/10* (2016.08); *A23L 33/115* (2016.08); *A23L 33/12* (2016.08); *A23L 33/125* (2016.08); *A23L 33/13* (2016.08); *A23L 33/155* (2016.08); *A23L 33/16* (2016.08); *A23L 33/17* (2016.08); *A23L 33/18* (2016.08); *A23L 33/19* (2016.08); *A23L 33/26* (2016.08); *A23L 33/40* (2016.08); *A61K 9/0053* (2013.01); *A61K 31/015* (2013.01); *A61K 31/05* (2013.01); *A61K 31/122* (2013.01); *A61K 31/14* (2013.01); *A61K 31/185* (2013.01); *A61K 31/194* (2013.01); *A61K 31/197* (2013.01); *A61K 31/201* (2013.01); *A61K 31/202* (2013.01); *A61K 31/203* (2013.01); *A61K 31/205* (2013.01); *A61K 31/355* (2013.01); *A61K 31/375* (2013.01); *A61K 31/4188* (2013.01); *A61K 31/455* (2013.01); *A61K 31/51* (2013.01); *A61K 31/519* (2013.01); *A61K 31/525* (2013.01); *A61K 31/593* (2013.01); *A61K 31/685* (2013.01); *A61K 31/702* (2013.01); *A61K 31/7004* (2013.01); *A61K 31/708* (2013.01); *A61K 31/7016* (2013.01); *A61K 31/7068* (2013.01); *A61K 31/7072* (2013.01); *A61K 31/7076* (2013.01); *A61K 31/714* (2013.01); *A61K 31/718* (2013.01); *A61K 31/733* (2013.01); *A61K 33/00* (2013.01); *A61K 33/04* (2013.01); *A61K 33/14* (2013.01); *A61K 33/26* (2013.01);
(Continued)

(58) Field of Classification Search
CPC .... A61K 38/38; A61K 38/40; A61K 31/7016; A61K 31/202; A61K 31/702; A23L 33/12; A23L 33/125; A23L 33/18; A23L 33/26; A23L 33/40; A23L 33/21; A23L 33/17
See application file for complete search history.

(56) References Cited

U.S. PATENT DOCUMENTS

| | | |
|---|---|---|
| 9,181,325 B2 | 11/2015 | Bertelsen et al. |
| 2006/0286252 A1 | 12/2006 | Rangavajla et al. |

(Continued)

FOREIGN PATENT DOCUMENTS

| | | |
|---|---|---|
| CN | 102283289 A | 12/2011 |
| CN | 102422900 A | 4/2012 |

(Continued)

OTHER PUBLICATIONS

O'Connor; "Infant Formula"; Am Fam Physician; 2009;79(7):565-570 (Year: 2009).*

(Continued)

*Primary Examiner* — Timothy P Thomas
(74) *Attorney, Agent, or Firm* — Wolf, Greenfield & Sacks, P.C.

(57) ABSTRACT

The present disclosure provides a nutritional formula comprising alpha-lactalbumin enriched whey protein concentrate; beta-casein enriched milk protein; mildly hydrolyzed milk protein; osteopontin; lactoferrin; oleic acid-palmitic acid-oleic acid triglyceride, wherein palmitic acid is at the SN-2 position of the glycerol backbone of the triglyceride; lactose, wherein the lactose is reduced lactose; lutein; docosahexanoic acid; arachidonic acid; galactooligosaccharides; and polydextrose. The provided nutritional formulas may be useful in providing nutrition and/or promoting postnatal development of a subject (e.g., promoting postnatal development of an infant's gastrointestinal functions, nutrient absorption, immune system development, etc.). Also provided are powder forms, reconstituted formulas, kits, methods, and uses that include or involve a nutritional formula described herein.

25 Claims, No Drawings

(51) Int. Cl.

| | |
|---|---|
| A23L 33/26 | (2016.01) |
| A23L 33/125 | (2016.01) |
| A23L 33/18 | (2016.01) |
| A23L 33/19 | (2016.01) |
| A23L 33/00 | (2016.01) |
| A23L 33/17 | (2016.01) |
| A23L 33/10 | (2016.01) |
| A23L 33/115 | (2016.01) |
| A23L 33/13 | (2016.01) |
| A23L 33/16 | (2016.01) |
| A23L 33/155 | (2016.01) |
| A61K 9/00 | (2006.01) |
| A61K 31/015 | (2006.01) |
| A61K 31/05 | (2006.01) |
| A61K 31/122 | (2006.01) |
| A61K 31/14 | (2006.01) |
| A61K 31/185 | (2006.01) |
| A61K 31/194 | (2006.01) |
| A61K 31/197 | (2006.01) |
| A61K 31/201 | (2006.01) |
| A61K 31/202 | (2006.01) |
| A61K 31/203 | (2006.01) |
| A61K 31/205 | (2006.01) |
| A61K 31/355 | (2006.01) |
| A61K 31/375 | (2006.01) |
| A61K 31/4188 | (2006.01) |
| A61K 31/455 | (2006.01) |
| A61K 31/51 | (2006.01) |
| A61K 31/519 | (2006.01) |
| A61K 31/525 | (2006.01) |
| A61K 31/593 | (2006.01) |
| A61K 31/685 | (2006.01) |
| A61K 31/7004 | (2006.01) |
| A61K 31/7016 | (2006.01) |
| A61K 31/702 | (2006.01) |
| A61K 31/7068 | (2006.01) |
| A61K 31/7072 | (2006.01) |
| A61K 31/7076 | (2006.01) |
| A61K 31/708 | (2006.01) |
| A61K 31/714 | (2006.01) |
| A61K 31/718 | (2006.01) |
| A61K 31/733 | (2006.01) |
| A61K 33/00 | (2006.01) |
| A61K 33/04 | (2006.01) |
| A61K 33/14 | (2006.01) |
| A61K 33/26 | (2006.01) |
| A61K 33/30 | (2006.01) |
| A61K 33/32 | (2006.01) |
| A61K 33/34 | (2006.01) |
| A61K 33/42 | (2006.01) |
| A61K 38/17 | (2006.01) |
| A61K 38/40 | (2006.01) |

(52) U.S. Cl.
CPC .............. *A61K 33/30* (2013.01); *A61K 33/32* (2013.01); *A61K 33/34* (2013.01); *A61K 33/42* (2013.01); *A61K 38/1709* (2013.01); *A61K 38/40* (2013.01); *A23V 2002/00* (2013.01)

(56) References Cited

U.S. PATENT DOCUMENTS

| | | |
|---|---|---|
| 2012/0171328 A1 | 7/2012 | Banavara et al. |
| 2014/0037818 A1* | 2/2014 | Sorensen ................ A23L 33/40 426/580 |
| 2015/0189905 A1 | 7/2015 | Banavara et al. |
| 2015/0237902 A1 | 8/2015 | Rosado Loria et al. |
| 2016/0015068 A1* | 1/2016 | Ao ......................... A23L 33/40 426/61 |
| 2021/0386107 A1 | 12/2021 | McGrath et al. |

FOREIGN PATENT DOCUMENTS

| | | |
|---|---|---|
| CN | 104489101 A | 4/2015 |
| CN | 105638908 A | 6/2016 |
| EP | 2208424 A1 | 7/2010 |
| JP | S53-079060 A | 7/1978 |
| JP | S56-36494 A | 4/1981 |
| JP | H05-236883 A | 9/1993 |
| JP | H05-268879 A | 10/1993 |
| JP | H07-508417 A | 9/1995 |
| JP | 2004-519229 A | 7/2004 |
| JP | 2007-505610 A | 3/2007 |
| JP | 2014-508157 A | 4/2014 |
| RU | 2013125292 A | 12/2014 |
| RU | 2575610 C2 * | 2/2016 |
| RU | 2575610 C2 | 2/2016 |
| WO | 2011/051557 A1 | 5/2011 |
| WO | 2012/092157 A2 | 7/2012 |
| WO | 2015/154265 A1 | 10/2015 |
| WO | 2016/010664 A1 | 1/2016 |
| WO | 2017/102710 A1 | 6/2017 |
| WO | 2018/009647 A1 | 1/2018 |

OTHER PUBLICATIONS

Moreau et al.; "A Comparison of the Levels of Lutein and Zeaxanthin in Corn Germ Oil, Corn Fiber Oil and Corn Kernel Oil"; 2007; J. Am. Oil Chem. Soc.; 84:1039-1044 (Year: 2007).*
Raninen et al.; "Dietary fiber type reflects physiological functionality: comparison of grain fiber, inulin, and polydextrose"; 2011; Nutrition Reviews; vol. 69(1):9-21; doi: 10.1111/j.1753-4887.2010.00358.x (Year: 2011).*
EP 17824875.3, Dec. 13, 2019, Partial Supplementary European Search Report.
EP 17824875.3, Mar. 16, 2020, Extended European Search Report.
PCT/US2017/040879, Sep. 28, 2017, International Search Report and Written Opinion.
PCT/US2017/040879, Jan. 17, 2019, International Preliminary Report on Patentability.
Partial Supplementary European Search Report, in connection with Application No. EP 17824875.3, dated Dec. 13, 2019.
Extended European Search Report, in connection with Application No. EP 17824875.3, dated Mar. 16, 2020.
International Search Report and Written Opinion, in connection with Application No. PCT/US2017/040879, dated Jan. 17, 2019.
International Preliminary Report on Patentability, in connection with Application No. PCT/US2017/040879, dated Sep. 28, 2017.
[No Author Listed] Database GNPD: Accession No. 1480298. Baby Milk Stage 1. Feb. 9, 2011. Retrieved from https://www.gnpd.com. 4 pages.
[No Author Listed] Database GNPD: Accession No. 2170047. Baby Formula Kit. Sep. 13, 2013. Retrieved from https://www.gnpd.com. 7 pages.
[No Author Listed] Database WPI Week 201539. Thomson Scientific. AN 2015-342709. CN 104 489 101 A (Ausnutria Dairy China Co LTD). Apr. 8, 2015. 2 pages.
[No Author Listed] Database WPI Week 201670. Thomson Scientific. An 2016-38070M. CN 105 638 908 A (Univ Northeast Agricultural). Jun. 8, 2016. 2 pages.
Gopal et al., Oligosaccharides and glycoconjugates in bovine milk and colostrum. Br J Nutr. 2000;84 Suppl 1:S69-S74. doi:10.1017/s0007114500002270.
International Search Report and Written Opinion for Application No. PCT/US2021/037403, dated Sep. 15, 2021.
[No Author Listed], Gerber® Good Start® Gentle. Gerber. Accessed 2014 from <https://medical.gerber.com/products/formulas/good-start-gentle>. 4 pages.

(56) References Cited

OTHER PUBLICATIONS

Agostoni et al., Neurodevelopmental quotient of healthy term infants at 4 months and feeding practice: the role of long-chain polyunsaturated fatty acids. Pediatr Res. Aug. 1995;38(2):262-6. doi: 10.1203/00006450-199508000-00021.
Auestad et al., Visual acuity, erythrocyte fatty acid composition, and growth in term infants fed formulas with long chain polyunsaturated fatty acids for one year. Ross Pediatric Lipid Study. Pediatr Res. Jan. 1997;41(1):1-10. doi: 10.1203/00006450-199701000-00001.
Ballard et al., Human milk composition: nutrients and bioactive factors. Pediatr Clin North Am. Feb. 2013;60(1):49-74. doi: 10.1016/j.pcl.2012.10.002. Author Manuscript. 24 pages.
Birch et al., A randomized controlled trial of early dietary supply of long-chain polyunsaturated fatty acids and mental development in term infants. Dev Med Child Neurol. Mar. 2000;42(3):174-81. doi: 10.1017/s0012162200000311.
Bode, Human milk oligosaccharides: every baby needs a sugar mama. Glycobiology. Sep. 2012;22(9):1147-62. doi: 10.1093/glycob/cws074. Epub Apr. 18, 2012.
Brenna et al., Docosahexaenoic and arachidonic acid concentrations in human breast milk worldwide. Am J Clin Nutr. Jun. 2007;85(6):1457-64. doi: 10.1093/ajcn/85.6.1457.
Capeding et al., Lutein-fortified infant formula fed to healthy term infants: evaluation of growth effects and safety. Nutr J. May 21, 2010;9:22. doi: 10.1186/1475-2891-9-22.
Cheng et al., Factors affecting the lactoferrin concentration in bovine milk. J Dairy Sci. Mar. 2008;91(3):970-6. doi: 10.3168/jds.2007-0689.
Clandinin et al., Extrauterine fatty acid accretion in infant brain: implications for fatty acid requirements. Early Hum Dev. Jun. 1980;4(2):131-8. doi: 10.1016/0378-3782(80)90016-x.
Clandinin et al., Intrauterine fatty acid accretion rates in human brain: implications for fatty acid requirements. Early Hum Dev. Jun. 1980;4(2):121-9. doi: 10.1016/0378-3782(80)90015-8.
Coppa et al., Oligosaccharides in human milk during different phases of lactation. Acta Paediatr Suppl. Aug. 1999;88(430):89-94. doi: 10.1111/j.1651-2227.1999.tb01307.x.
Dupont et al., Alpha-lactalbumin-enriched and probiotic-supplemented infant formula in infants with colic: growth and gastrointestinal tolerance. Eur J Clin Nutr. Jul. 2010;64(7):765-7. doi: 10.1038/ejcn.2010.81. Epub Jun. 2, 2010.
Innis et al., Evidence that palmitic acid is absorbed as sn-2 monoacylglycerol from human milk by breast-fed infants. Lipids. Aug. 1994;29(8):541-5. doi: 10.1007/BF02536625.
Innis, Dietary triacylglycerol structure and its role in infant nutrition. Adv Nutr. May 2011;2(3):275-83. doi: 10.3945/an.111.000448. Epub Apr. 30, 2011.
Johnston et al., Growth and tolerance of formula with lactoferrin in infants through one year of age: double-blind, randomized, controlled trial. BMC Pediatr. Nov. 7, 2015;15:173. doi: 10.1186/s12887-015-0488-3.
Kennedy et al., Double-blind, randomized trial of a synthetic triacylglycerol in formula-fed term infants: effects on stool biochemistry, stool characteristics, and bone mineralization. Am J Clin Nutr. Nov. 1999;70(5):920-7. doi: 10.1093/ajcn/70.5.920.
King, Jr, et al., A double-blind, placebo-controlled, pilot study of bovine lactoferrin supplementation in bottle-fed infants. J Pediatr Gastroenterol Nutr. Feb. 2007;44(2):245-51. doi: 10.1097/01.mpg.0000243435.54958.68.
Krinsky et al., Carotenoid actions and their relation to health and disease. Mol Aspects Med. Dec. 2005;26(6):459-516. doi: 10.1016/j.mam.2005.10.001. Epub Nov. 23, 2005.

Landrum et al., Lutein, zeaxanthin, and the macular pigment. Arch Biochem Biophys. Jan. 1, 2001;385(1):28-40. doi: 10.1006/abbi.2000.2171.
Lien et al., Growth and safety in term infants fed reduced-protein formula with added bovine alpha-lactalbumin. J Pediatr Gastroenterol Nutr. Feb. 2004;38(2):170-6. doi: 10.1097/00005176-200402000-00013.
Lien, The role of fatty acid composition and positional distribution in fat absorption in infants. J Pediatr. Nov. 1994;125(5 Pt 2):S62-8. doi: 10.1016/s0022-3476(06)80738-9.
Litmanovitz et al., Reduced crying in term infants fed high beta-palmitate formula: a double-blind randomized clinical trial. BMC Pediatr. Jun. 19, 2014;14:152. doi: 10.1186/1471-2431-14-152.
Lönnerdal, Digestibility and absorption of protein in infants. In: Protein Metabolism During Infancy. Protein Metabol During Infancy. Raiha et al. Eds. 1994. pp. 53-65.
Lönnerdal, Infant formula and infant nutrition: bioactive proteins of human milk and implications for composition of infant formulas. Am J Clin Nutr. Mar. 2014;99(3):712S-7S. doi: 10.3945/ajcn.113.071993. Epub Jan. 22, 2014.
Mitchell et al., Protein efficiency ratios and net protein ratios of selected protein foods. Plant Foods Hum Nutr. 1989;39(1):53-8. doi: 10.1007/BF01092401.
Moro et al., Dosage-related bifidogenic effects of galacto- and fructooligosaccharides in formula-fed term infants. J Pediatr Gastroenterol Nutr. Mar. 2002;34(3):291-5. doi: 10.1097/00005176-200203000-00014.
Neuringer et al., Biochemical and functional effects of prenatal and postnatal omega 3 fatty acid deficiency on retina and brain in rhesus monkeys. Proc Natl Acad Sci USA. Jun. 1986;83(11):4021-5. doi: 10.1073/pnas.83.11.4021.
Ochoa et al., Effect of lactoferrin on enteric pathogens. Biochimie. Jan. 2009;91(1):30-4. doi: 10.1016/j.biochi.2008.04.006. Epub Apr. 18, 2008.
O'Connor et al., Growth and development in preterm infants fed long-chain polyunsaturated fatty acids: a prospective, randomized controlled trial. Pediatrics. Aug. 2001;108(2):359-71. doi: 10.1542/peds.108.2.359.
Roberfroid, Prebiotics: the concept revisited. J Nutr. Mar. 2007;137(3 Suppl 2):830S-7S. doi: 10.1093/jn/137.3.830S.
Scalabrin et al., New prebiotic blend of polydextrose and galacto-oligosaccharides has a bifidogenic effect in young infants. J Pediatr Gastroenterol Nutr. Mar. 2012;54(3):343-52. doi: 10.1097/MPG.0b013e318237ed95.
Schack et al., Considerable variation in the concentration of osteopontin in human milk, bovine milk, and infant formulas. J Dairy Sci. Nov. 2009;92(11):5378-85. doi: 10.3168/jds.2009-2360.
Tadesse, The effect of continued feeding of physiological amounts of lactose on the level of intestinal lactase and other disaccharidase enzyme activities in the rat. Exp Physiol. Mar. 1990;75(2):231-8. doi: 10.1113/expphysiol.1990.sp003397.
Trabulsi et al., Effect of an a-lactalbumin-enriched infant formula with lower protein on growth. Eur J Clin Nutr. Feb. 2011;65(2):167-74. doi: 10.1038/ejcn.2010.236. Epub Nov. 10, 2010.
Yao et al., Effects of term infant formulas containing high sn-2 palmitate with and without oligofructose on stool composition, stool characteristics, and bifidogenicity. J Pediatr Gastroenterol Nutr. Oct. 2014;59(4):440-8. doi: 10.1097/MPG.0000000000000443.
Ziegler et al., Term infants fed formula supplemented with selected blends of prebiotics grow normally and have soft stools similar to those reported for breast-fed infants. J Pediatr Gastroenterol Nutr. Mar. 2007;44(3):359-64. doi: 10.1097/MPG.0b013e31802fca8c.

* cited by examiner

NUTRITIONAL FORMULA

RELATED APPLICATIONS

This application is a national stage filing under 35 U.S.C. § 371 of international PCT application, PCT/US2017/040879, filed Jul. 6, 2017, which claims priority under 35 U.S.C. § 119(e) to U.S. Provisional Application, U.S. Ser. No. 62/359,033, filed Jul. 6, 2016, each of which is incorporated herein by reference.

BACKGROUND OF THE INVENTION

The focal point of infant nutrition is the developing gastrointestinal tract, and its response to the infant's feeding. The tolerance of the infant formula along with the postnatal development of gastrointestinal functions, nutrient absorption, immune system development, gut epithelia interactions and micro flora maintenance during digestion provide for the healthy development of the infant. This nutritional formula provides for one or more of these advantages.

Specifically, without wishing to be bound by any particular theory, mildly hydrolyzed skim milk solids and demineralized whey support the ease of digestion and full absorption of milk proteins. Beta casein improves the digestibility, improves tolerance (comfort), reduces food intolerances, and sensitivity intolerance. Oleic acid-palmitic acid-oleic acid triglyceride, wherein palmitic acid is at the SN-2 position of the glycerol backbone of the triglyceride ("OPO SN-2 oil"), improves the efficiency of fatty acid absorption, improves the digestibility, reduced calcium loss to infant stools, reduces the incidence of constipation, and improves calcium absorption. Lactoferrin helps support the infant immune system, intestinal development, and iron absorption. The combination of lutein and docosahexaenoic acid may promote retinal health and vision development. Docosahexaenoic acid is susceptible to damage by oxidation and degradation, while lutein is an antioxidant. Lutein may reduce oxidative degradation of docosahexaenoic acid concentrated in the retina, and thus further promote retinal health and vision development. Docosahexaenoic acid and arachidonic acid improve the tolerance and acceptance of the nutritional formula. Prebiotics are thought to modulate the gut flora, affect diverse gastrointestinal activities, and influence inflammatory processes.

SUMMARY OF THE INVENTION

A nutritional formula of the present invention provides a subject (e.g., infants) with nutrients similar to those provided by human breast milk while maintaining and promoting healthy gastrointestinal function in the subject (e.g., infant). Specifically, the addition of alpha-lactalbumin is thought to facilitate the absorption of essential minerals, and alpha-lactalbumin provides a well-balanced supply of essential amino acids to the subject (e.g., a growing infant) The addition of osteopontin lowers the total protein content of the infant formula to reduce the risk of later development of obesity in the subject administered the infant formula. Osteopontin is shown to reduce infection, can improve energy intake and is suggested to play a role in regulating immunity, whereby osteopontin in infant formula could deliver immune protection similar to that of human breastmilk.

A nutritional formulation of the present invention provides nutrition to subjects in need thereof (e.g., infants), similar to the nutrition provided by human breast milk. The present invention provides a nutritional formula comprising protein, lipid, carbohydrate, lutein, polyunsaturated fatty acids, and prebiotics. The invention provides for powder forms of the nutritional formula, reconstituted formulas, methods of administering the nutritional formula, and kits useful for administration of the nutritional formula to a subject. The present invention also provides methods of preparing the nutritional formula. The nutritional formulas described herein are useful in providing nutrition and/or promoting postnatal development of a subject (e.g., promoting postnatal development of an infant's gastrointestinal functions, nutrient absorption, immune system development, etc.) comprising feeding the subject with the nutritional formulas described herein.

In one aspect, the present disclosure provides a nutritional formula comprising: protein, lipid, carbohydrate, lutein, polyunsaturated fatty acids, and prebiotics. The invention provides for powder forms of the nutritional formula, reconstituted formulas, methods of administering the nutritional formula, and kits useful for administration of the nutritional formula to a subject, as defined herein. Specifically, the nutritional formula of the present invention includes ingredients for providing nutrition, including, but not limited to, alpha-lactalbumin enriched whey protein concentrate; beta-casein enriched milk protein; mildly hydrolyzed milk protein; lactoferrin; oleic acid-palmitic acid-oleic acid triglyceride, wherein palmitic acid is at the SN-2 position of the glycerol backbone of the triglyceride; lactose, wherein the lactose is reduced lactose; lutein; docosahexanoic acid; arachidonic acid; and prebiotics selected from galactooligosaccharides, polydextrose, inulin, human milk oligosaccharides, and combinations thereof. The nutritional formula of the present invention may also include vitamins, minerals, nucleotides, biotin, choline, inositol, taurine, L-carnitine, or combinations thereof. A nutritional formula with improved tolerance, while providing for nutrition and postnatal development gastrointestinal functions, nutrient absorption, and healthy immune system development for a subject (e.g., an infant) is needed.

In one aspect, the present disclosure provides a nutritional formula comprising: protein, lipid, carbohydrate, lutein, polyunsaturated fatty acids, and prebiotics. The invention provides for powder forms of the nutritional formula, reconstituted formulas, methods of administering the nutritional formula, and kits useful for administration of the nutritional formula to a subject, as defined herein. Specifically, the nutritional formula of the present invention includes ingredients for providing nutrition, including, but not limited to, alpha-lactalbumin enriched whey protein concentrate; skimmed milk powder; osteopontin; lactoferrin; oleic acid-palmitic acid-oleic acid triglyceride, wherein palmitic acid is at the SN-2 position of the glycerol backbone of the triglyceride; lactose, wherein the lactose is reduced lactose; lutein; docosahexanoic acid; arachidonic acid; and prebiotics selected from galactooligosaccharides, polydextrose, inulin, fructooligosaccharides, human milk oligosaccharides, and combinations thereof. The nutritional formula of the present invention may also include vitamins, minerals, nucleotides, biotin, choline, inositol, taurine, L-carnitine, or combinations thereof. A nutritional formula with improved tolerance, while providing for nutrition and postnatal development gastrointestinal functions, nutrient absorption, and healthy immune system development for a subject (e.g., an infant) is needed.

Exemplary nutritional formulas include, but are not limited to, a nutritional formula comprising alpha-lactalbumin enriched whey protein concentrate; beta-casein enriched milk protein; mildly hydrolyzed milk protein; lactoferrin; oleic acid-palmitic acid-oleic acid triglyceride, wherein palmitic acid is at the SN-2 position of the glycerol backbone of the triglyceride; lactose, wherein the lactose is reduced lactose; lutein; docosahexanoic acid; arachidonic acid; galactooligosaccharides; and polydextrose, and powder forms and reconstituted formulas thereof. In certain embodiments exemplary nutritional formulas include, but are not limited to, a nutritional formula comprising alpha-lactalbumin enriched whey protein concentrate; osteopontin; lactoferrin; oleic acid-palmitic acid-oleic acid triglyceride, wherein palmitic acid is at the SN-2 position of the glycerol backbone of the triglyceride; lactose, wherein the lactose is reduced lactose; lutein; docosahexanoic acid; arachidonic acid; galactooligosaccharides; and polydextrose, and powder forms and reconstituted formulas thereof.

In another aspect, described herein are reconstituted formulas including a powder form of the nutritional formula described herein, reconstituted with water to form a ready-to-feed liquid. The reconstituted formulas may be useful in providing nutrition and/or promoting postnatal development of a subject (e.g., promoting development of an infant's gastrointestinal functions, nutrient absorption, immune system development, etc.).

In another aspect, described herein are methods of providing nutrition (e.g., feeding) to a subject (e.g., an infant) comprising administering the nutritional formula described herein to the subject. In another aspect, described herein are methods of providing nutrition to (e.g., feeding) a subject (e.g., an infant) comprising reconstituting a powdered form of the nutritional formula described herein with water to form a ready-to-feed liquid, and feeding the reconstituted formula to a subject. In another aspect, described herein are uses of the nutritional formula described herein for providing nutrition as well as postnatal development of gastrointestinal functions, promoting nutrient absorption, immune system development, and combinations thereof.

In certain embodiments, the subject being administered a nutritional formula described herein is a human (e.g., an infant not more than about two years of age, or a newborn). In certain embodiments, the subject being administered a nutritional formula described herein is a non-human animal.

In still another aspect, described herein are kits including a container with a nutritional formula described herein. A kit described herein may include a single serving or multiple servings (e.g., one or more packages of the powdered nutritional formula described herein) of the nutritional formula or reconstituted formula. The described kits may be useful in providing nutrition and/or promoting postnatal development of a subject (e.g., promoting postnatal development of an infant's gastrointestinal functions, nutrient absorption, immune system development, etc.). In certain embodiments, a kit described herein further includes instructions for using the kit. In still another aspect, described herein are devices (e.g., bottles) for feeding a subject with the nutritional formula or reconstituted formula.

The present application refers to various issued patent, published patent applications, journal articles, and other publications, all of which are incorporated herein by reference. The details of one or more embodiments of the invention are set forth herein. Other features, objects, and advantages of the invention will be apparent from the Detailed Description, the Examples, and the claims.

Definitions

Definitions of specific nutritional terms and chemical terms are described in more detail below.

The term "nutritional formula" as used herein refers to a nutritional composition that is designed for the administration of sufficient fat, protein, carbohydrate, vitamins, minerals, prebiotics, and other nutrients to a subject. The nutritional formula may be the sole source of nutrition when provided in sufficient quantity. The nutritional formula is suitable for consumption by a subject in need thereof as described herein, including, but not limited to, infants.

The term "formula" encompasses any form of the nutritional formula described herein, including, but not limited to, powder and liquid formulae. Additionally, the powder can be reconstituted from a dehydrated powder form to yield a liquid form suitable for the administration of the formula to a subject, including an infant.

The term "ready-to-feed" used herein refers to a liquid formula suitable for administration to a subject, including reconstituted powders, diluted formulas of a concentrated nutritional formula, and manufactured liquids.

As used herein, concentrations expressed as micrograms per liter ("mcg/L"), milligrams per liter ("mg/L"), and grams per liter ("g/L") refer to ingredient concentrations within the nutritional formulation of the present invention calculated on a reconstituted, ready-to-feed, or fed basis, unless otherwise specified.

The term "about X," or "approximately X," where X is a number or percentage, refers to a number or percentage that is between 99.5% and 100.5%, between 99% and 101%, between 98% and 102%, between 97% and 103%, between 96% and 104%, between 95% and 105%, between 92% and 108%, or between 90% and 110%, inclusive, of X.

As used herein, a "subject" is a mammal. In certain embodiments, the mammal is an animal. In certain embodiments, the animal is a human. In certain embodiments, the human is an adult, adolescent, child, toddler, infant, or newborn of either sex. An "infant" or "newborn" refers to a human not more than about two years of age. The term "infant" also includes an infant from about 0 to about 4 months of age, from about 4 to about 8 months of age, from about 8 to about 12 months of age, from about 12 to about 16 months of age, from about 16 to about 18 months of age, and from about 18 to about 24 months of age, and preterm infants that are less than about 37 weeks gestational age. A "newborn" is an infant that is not more than about 4 weeks of age, and includes an infant from about 0 to about 1 week of age, from about 1 to about 2 weeks of age, from about 2 to about 3 weeks of age, and from about 3 to about 4 weeks of age. In certain embodiments, the animal is non-human. In certain embodiments, the non-human animal is a cow, sheep, buffalo, goat, camel, donkey, horse, or any other non-human animal that produces milk.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long.

"Whey protein concentrate" is a concentrated form of whey protein. The term whey protein concentrate encompasses whey protein of any size, structure, or function, and from any source or any composition. In nutrition, whey protein concentrate may be used to increase dietary protein intake. In general, whey protein concentrate contains from about 20% to about 90% protein by weight.

"Demineralized whey" or "reduced-minerals whey" refers to, with reference to a purification process, whey protein in which the minerals and salts (organic and inorganic) have been removed. In some embodiments, between 25-90% of the minerals in the whey protein in the demineralized whey are removed. In some embodiments, up to 25% of the minerals in the whey protein in the demineralized whey are removed. In some embodiments, up to 50% of the minerals in the whey protein in the demineralized whey are removed. In some embodiments, up to 60% of the minerals in the whey protein in the demineralized whey are removed. In some embodiments, up to 75% of the minerals in the whey protein in the demineralized whey are removed. In some embodiments, up to 80% of the minerals in the whey protein in the demineralized whey are removed. In some embodiments, up to 90% of the minerals in the whey protein in the demineralized whey are removed.

The term "mildly hydrolyzed milk protein" refers to a milk protein hydrolysate with a low level of hydrolysis. In some embodiments, the mildly hydrolyzed milk protein is a milk protein hydrolysate that is up to 2.0% hydrolyzed. In some embodiments, the mildly hydrolyzed milk protein is a milk protein hydrolysate that is up to 1.75% hydrolyzed. In some embodiments, the mildly hydrolyzed milk protein is a milk protein hydrolysate that is up to 1.5% hydrolyzed. In some embodiments, the mildly hydrolyzed milk protein is a milk protein hydrolysate that is up to 1.25% hydrolyzed. In some embodiments, the mildly hydrolyzed milk protein is a milk protein hydrolysate that is up to 1.0% hydrolyzed. In some embodiments, the mildly hydrolyzed milk protein is a milk protein hydrolysate that is up to 0.75% hydrolyzed. In some embodiments, the mildly hydrolyzed milk protein is a milk protein hydrolysate that is up to 0.5% hydrolyzed. In some embodiments, the mildly hydrolyzed milk protein is a milk protein hydrolysate that is up to 0.25% hydrolyzed. In some embodiments, the mildly hydrolyzed milk protein is a milk protein hydrolysate that is up to 0.1% hydrolyzed.

The term "skimmed milk powder" refers to a product that results from the removal of fat and water from pasteurized milk. The term skimmed milk powder also encompasses "skim milk powder." In skimmed milk powder, the fat content or protein content or both in the milk can be altered by the removal or addition of milk constituents. Milk retentate, milk permeate, and lactose can be used to adjust the skimmed milk powder protein content. Skimmed milk powder retains the original whey protein to casein ratio present in the milk. The production of skimmed milk powder often involves, but is not limited to, the evaporation of moisture from the milk until a dry powder with a low moisture content is obtained. The milk used to produce the skimmed milk powder as described herein can be obtained from any source. As described herein, skimmed milk powder can be obtained from any source.

"Osteopontin" is an extracellular structural protein expressed in bone and other tissues and body fluids. The term osteopontin also encompasses "OPN," "bone sialoprotein I," "BSPI," "BNSP," "early T-lymphocyte activation," "ETA-1," "secreted phosphoprotein 1" and "SPP1". As described herein, osteopontin can be obtained from any source. Osteopontin influences the development and maintenance of immune response by affecting the function of immune cells, such as macrophages, dendritic cells, and T-cells. Osteopontin can enhance host resistance to infection and enhance bacterial phagocytosis. Human breast milk contains a significantly higher amount of osteopontin than bovine milk or traditional infant formula. In nutrition, osteopontin content in infant formula may facilitate immune system development in a human (e.g., an infant not more than about two years of age, or a newborn).

"Alpha-lactalbumin" "α-lactalbumin" is the major protein in human breast milk, constituting between about 20% to about 25% of the total protein content. The alpha-lactalbumin protein binds divalent cations, such as $Ca^{2+}$ and $Zn^{2+}$, in addition to aiding in the absorption of essential dietary minerals. Upon digestion within the gastrointestinal tract, alpha-lactalbumin derived peptides may exhibit antibacterial and immune stimulatory properties to protect the subject against infection. As described herein, the alpha-lactalbumin can be obtained from any source.

The term "enriched" refers to a protein fraction having a high amount of a specified protein. In some embodiments, the protein fraction enriched with a specified protein has at least 30% of the specified enriched protein. In some embodiments, the protein fraction enriched with a specified protein has at least 40% of the specified protein. In some embodiments, the protein fraction enriched with a specified protein has at least 50% of the specified protein. In some embodiments, the protein fraction enriched with a specified protein has at least 60% of the specified protein. In some embodiments, the protein fraction enriched with a specified protein has at least 65% of the specified protein. In some embodiments, the protein fraction enriched with a specified protein has at least 70% of the specified protein. In some embodiments, the protein fraction enriched with a specified protein has at least 80% of the specified protein. In some embodiments, the protein fraction enriched with a specified protein has at least 90% of the specified protein. "Alpha-lactalbumin enriched whey protein concentrate" or "alpha-lactalbumin enhanced whey protein concentrate" refers to a whey protein concentrate fraction is enriched with alpha-lactalbumin.

"Beta-casein" or "β-casein" is a common phosphoprotein in mammalian milk. The casein content provided by the nutritional formula described herein contains beta-casein enriched milk protein fractions, which brings the total casein close to that of human breast milk. Beta-casein improves the digestibility and tolerance of nutritional formula. Upon digestion, the peptides provided by partially hydrolyzed beta-casein aid in the utilization of macronutrients and micronutrients, as well as impart protection against pathogenic bacteria found in the gut. As described herein, the beta-casein can be obtained from any source. "Beta-casein enriched milk protein" refers to a milk protein fraction that is enriched with beta-casein.

"Lactoferrin" is a protein produced during the late stages of pregnancy and is found in breast milk colostrum and mature breast milk. Lactoferrin is classified as a glycoprotein, in which normally about 1 to about 4 glycans are attached to amino acid side chains throughout the protein. Lactoferrin aids in intestinal development and iron absorption, as well as provides immune system support. As described herein, the lactoferrin can be obtained from any source.

A "fat," "triglyceride," "lipid," or "oil" is comprised of three fatty acid chains connected to a glycerol molecule through an ester bond. The term fat refers to all fat, triglyceride, and oil molecules of any size, structure, or function. Typically, a fat is a hydrophobic molecule that is insoluble in water. An oil is generally an unsaturated fatty acid chains. Fats may include fatty acid chains that are either saturated or unsaturated. A saturated fat contains no double bonds between carbon atoms in the chain. An unsaturated fat contains one or more double bonds between carbon atoms in the chain, and the double bond or bonds can be in the cis or trans configuration. Fats containing one or more trans double bonds are called trans fats. Fat containing one or more cis double bonds are called cis fats. Further, a monounsaturated fatty acid contains at least one double bond between carbons in the aliphatic chain. A polyunsaturated fat that contains at least one aliphatic chains with at least two or more double bonds between carbons in the chain. Sources of fat and oils, including saturated, unsaturated, and polyunsaturated fat, include, but are not limited to, canola, sunflower, sesame, peanut, walnut, chia, palm, coconut, avocado, olive, safflower, seaweed, sardine, soybean, tuna, salmon, and whole grain wheat.

The term "unsaturated bond" refers to a double or triple bond.

The term "saturated" refers to a moiety that does not contain a double or triple bond, i.e., the moiety only contains single bonds.

A "fatty acid" is an aliphatic carbon chain connected to a carboxylic acid. The term fatty acid refers to fatty acids of any size, structure, or function. The aliphatic carbon chain may be either unsaturated or saturated. In some embodiments, the fatty acid is not connected to a glycerol backbone. A saturated fatty acid contains no double bonds between carbons in the chain. An unsaturated fatty acids contains one or more double bonds between carbons in the chain, and the double bond or bonds can be cis or trans. A monounsaturated fatty acid contains at least one double bond between carbons in the aliphatic chain. A polyunsaturated fatty acid contains at least two or more double bonds between carbons in the aliphatic chain. Fatty acids are generally straight-chained carbons and not branched carbon chains, wherein the number of carbon atoms present in the aliphatic chain is from 4 to about 28 carbon atoms. Fatty acid chains differ in length, wherein short-chain fatty acids (SCFA) are fatty acids with aliphatic chains of fewer than about 6 carbon atoms, wherein medium-chain fatty acids (MCFA) are fatty acids with aliphatic chains of about 6 to about 12 carbon atoms, wherein long-chain fatty acids (LCFA) are fatty acids with aliphatic chains of about 13 to about 21 carbon atoms, and wherein very long-chain fatty acids (VLCFA) are fatty acids with aliphatic chains of about 22 or more carbon atoms.

The term "aliphatic" refers to alkyl, alkenyl, alkynyl, and carbocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$) group. In certain embodiments, the alkyl group is a substituted $C_{1-10}$ alkyl group.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is unspecified (e.g., —CH=CHCH₃ or

may be an (E)- or (Z)-double bond.

Unsaturated fatty acids can be further classified according to the location of the double bond in the aliphatic carbon chain. The placement of the double bond is described by the number of the first carbon in the double bond, counting from the terminal methyl (—$CH_3$) of the aliphatic chain according to the formula below:

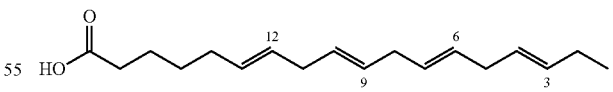

An "omega-3 fatty acid," "ω-3 fatty acid," or "n-3 fatty acid" contains a double bond at carbon 3. An "omega-6 fatty acid," "ω-6 fatty acid," or "n-6 fatty acid" contains a double bond at carbon 6. An "omega-9 fatty acid," "ω-9 fatty acid," or "n-9 fatty acid" contains a double bond at carbon 9. An "omega-12 fatty acid," "ω-12 fatty acid," or "n-12 fatty acid" contains a double bond at carbon 12.

"Oleic acid" or "C18:1" is a naturally occurring fatty acid in a variety of animal and vegetable oils. The term oleic acid as described herein encompasses fatty acids under the IUPAC nomenclature "(9E)-octadec-9-enoic acid." Oleic acid includes salts or esters of oleic acid, and is from any source. Oleic acid is further classified as an omega-9 cis monounsaturated fatty acid with one double bond at carbon 9 and a total of 18 carbons in the aliphatic chain (18:1 cis-9).

"Palmitic acid" or "C16:0" is the most common fatty acid found in animals, plants, and microorganisms, such as algae and fungi. The term palmitic acid as described herein encompasses all fatty acids under the IUPAC nomenclature "hexadecanoic acid." Palmitic acid includes salts or esters of palmitic acid, and is from any source. Palmitic acid is further classified as a saturated fatty acid and consists of a 16 carbon aliphatic chain (16:0).

"OPO SN-2 oil," "OPO" or "oleic acid-palmitic acid-oleic acid triglyceride" refers to an oleic acid-palmitic acid-oleic acid triglyceride, wherein palmitic acid is at the SN-2 position of the glycerol backbone of the triglyceride. In some embodiments, the oleic acid-palmitic acid-oleic acid triglyceride is of Formula (I):

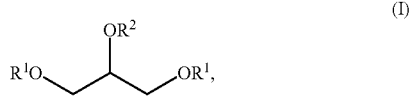

(I)

wherein $R^1$ is oleic acid (C18:1), and $R^2$ is palmitic acid (C16:0). In some embodiments, the SN-2 position of the glycerol backbone of the triglyceride is the second position on the glycerol backbone of the triglyceride. OPO SN-2 oil may refer to the oleic acid-palmitic acid-oleic acid triglyceride of Formula (I). Optionally, the fatty acid side chain may also be attached to the first position (SN-1) of the glycerol backbone. Optionally, the fatty acid side chain may be attached to the third position (SN-3) of the glycerol backbone. Optionally, about 50% to about 100% of the triglycerides in the OPO SN-2 oil are SN-2 triglycerides.

"Microencapsulated," "microencapsulation," or "microcapsule" refers to any substance, particle, or droplet surrounded by a coating of any material to give small capsules or the process of producing such capsules. Optionally, the coating material may include a carbohydrate (e.g., ethyl cellulose or sodium alginate), alcohol (e.g., polyvinyl alcohol), protein (e.g., sodium alginate), or combinations thereof. The term microencapsulated may refer to any food ingredient, enzyme, cell, or other material that may be incorporated into the relevant composition, mixture, ingredient, or product. Microencapsulation may be used to enclose any solid, liquid, or gaseous substance. Optionally, the microcapsule may be used to enclose any substance permanently or temporarily. The term microencapsulation covers all physical, chemical, and physiochemical techniques used in the process of generating microcapsules, including pan coating, air-suspension coating, centrifugal extrusion, vibrational nozzle, spray-drying, ionotropic gelation, coacervation-phase separation, interfacial polycondensation, interfacial cross-linking, in-situ polymerization, matrix polymerization, or the combination of techniques described herein.

"Docosahexaenoic acid" or "DHA" is an omega-3 fatty acid comprising a 22 carbon chain and 6 cis double bonds. The terms docosahexaenoic acid and DHA also encompass "cervonic acid," "all-cis-docosa-4,7,10,13,16,19-hexaenoic acid," "22:6(n-3)," and any fatty acid that can be classified under the IUPAC nomenclature "(4Z,7Z,10Z,13Z,16Z,19Z)-docosa-4,7,10,13,16,19-hexaenoic acid" and "doconexent". The terms docosahexaenoic acid and DHA may refer to any docosahexaenoic acid of any size, structure, or function. The docosahexaenoic acid defined herein may be from any source, including milk and/or oil, or a combination thereof. In certain embodiments, the milk is maternal milk, breast milk, and any combination thereof. In certain embodiments, the oil is fish oil, algae oil, microalgae oil, and any combination thereof. In certain embodiments, the docosahexaenoic acid is sourced from *Crypthecodinium cohnii* oil. In certain embodiments, the docosahexaenoic acid is sourced from fish oil. In certain embodiments, the docosahexaenoic acid is microencapsulated.

"Arachidonic acid" or "ARA" is a polyunsaturated omega-6 fatty acid comprising a 20 carbon aliphatic chain and 4 cis double bonds. The terms arachidonic acid and ARA also encompass "(5Z,8Z,11Z,14Z)-Icosa-5,8,11,14-tetraenoic acid," "5,8,11,14-all-cis-eicosatetraenoic acid," "all-cis-5,8,11,14-eicosatetraenoic acid," "arachidonate," and any fatty acid that can be classified under the IUPAC nomenclature "(5Z,8Z,11Z,14Z)-5,8,11,14-eicosatetraenoic acid". The arachidonic acid defined herein may be from any source, including milk and/or oil, or a combination thereof. In certain embodiments, the milk is maternal milk, breast milk, and any combination thereof. In certain embodiments, the oil is fish oil, algae oil, microalgae oil, and any combination thereof. In certain embodiments, the arachidonic acid is sourced from *Mortierella alpina* oil. In certain embodiments, the arachidonic acid is microencapsulated.

A "carbohydrate," "saccharide," "sugar," or "starch" is a molecule comprised of carbon, hydrogen, and oxygen atoms. The term carbohydrate refers to all carbohydrate, saccharide, sugar, or starch molecules of any size, structure, or function. A carbohydrate can be a monosaccharide or a single sugar molecule. Two or more monosaccharides may be joined by one or more glycosidic bonds to produce higher order carbohydrates. A disaccharide is a carbohydrate comprised of two monosaccharides, an oligosaccharide is comprised of about 3 to about 10 monosaccharides, and a polysaccharide is comprised of about 10 or more monosaccharides. In certain embodiments, the carbohydrate is lactose, maltodextrin, corn syrup, corn syrup solids, and any combination thereof. In certain embodiments, the carbohydrate is lactose, maltodextrin, or any combination thereof.

"Lactose" is a disaccharide carbohydrate. Lactose contains a galactose moiety and a glucose moiety linked by a glycosidic bond. The term lactose refers to any lactose of any size, structure, or function. The term lactose also encompasses "milk sugar," "4-O-β-D-galactopyranosyl-D-glucose," and any carbohydrate classified under the IUPAC nomenclature "β-D-galactopyranosyl-(1→4)-D-glucose".

"Maltodextrin" is a polysaccharide comprising D-glucose units connected in chains of any length. Optionally, the maltodextrin chain is between about 2 to about 17 glucose units long, and may exists as a mixture of chain lengths between about 2 to about 17 glucose units long. The term maltodextrin encompasses any maltodextrin of any size, structure, or function, and from any source.

An "antioxidant" is a molecule that can prevent the oxidation of another molecule. The term antioxidant refers to all antioxidants of any size, structure, or function. An antioxidant functions to prevent chain reactions produced by free radicals, or any atom, ion, or molecule with an unpaired electron, that arise through a variety of natural, biological, and metabolic oxidation reactions. Antioxidants may be sulfur-containing compounds, such as glutathione, an enzyme, or a dietary antioxidant. Typical dietary antioxidants may include vitamin A, vitamin C, vitamin E, lutein, and others.

"Lutein" is a xanthophyll, a division of the carotenoid group, with a yellow pigment. The term lutein also encompasses "luteine," "trans-lutein," "(1R)-4-[(1E,3E,5E,7E,9E,11E,13E, 15E,17E)-18-[(1R,4R)-4-hydroxy-2,6,6-trimethylcyclohex-2-en-1-yl]-3,7,12,16-tetramethyloctadeca-1,3,5,7,9,11,13,15,17-nonaenyl]-3,5,5-trimethylcyclohex-3-en-1-ol," and any xanthophyll or carotenoid that can be classified under the IUPAC nomenclature "β,ε-carotene-3,3'-diol." The term lutein encompasses any maltodextrin of any size, structure, or function, and from any source.

"Prebiotic" or "prebiotics" refers to a compound that may induce the growth and beneficial activity of host microorganisms, such as bacteria, fungi, or others. A prebiotic refers to all prebiotics of any size, structure, or function. A prebiotic may be from plant or animal sources. A prebiotic may be from human milk. In nutrition, a prebiotic is commonly a compound comprising dietary fiber, wherein the dietary fiber contains a soluble portion and an insoluble portion, and the fiber aids in digestion. A prebiotic commonly alters and effects the microorganisms living in the gastrointestinal tract of the host, and often influences microorganisms or microflora in the gut and elsewhere in the body. Prebiotics suitable for nutritional formulas include, but are not limited to, galactooligosaccharides, inulin, fructooligosaccharides, polydextrose, and human milk oligosaccharides including sialyllacto-N-tetraose, lactodifucotetraose, 3'-sialyllactose, 6'-sialyllactose, 3'-fucosyllactose, lacto-N-(neo)tetraose, lacto-N-fucopentaose, and 2'-fucosyllactose. Preferably, the nutritional composition contains galactooligosaccharides, polydextrose, or any combination thereof. Optionally, the nutritional formula includes galactooligosaccharides, polydextrose, and one or more additional prebiotics.

A "vitamin" or "nutrient" is an organic or inorganic compound that is required by an organism. The term vitamin refers to a vitamin or nutrient of any size, structure, or function. The term vitamin may also refer to a vitamin within a complex or coenzyme. Vitamins are any compound required by an organism that the organism cannot synthesize for itself and must be obtained from the organism's diet. Vitamins required by humans may include, but are not limited to, vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin $K_1$, folic acid, inositol, biotin, niacin, and the chemical nomenclature derivatives or variants of these named vitamins.

A "dietary mineral," "mineral," "trace mineral," "dietary element," or "mineral nutrient" is any chemical element required by living organisms. The term mineral or dietary mineral refers to a dietary mineral, dietary element, or mineral nutrient of any size, structure, or function. A dietary mineral does not include carbon, hydrogen, oxygen, or nitrogen due to their presence in common organic molecules. Dietary minerals important for humans include, but are not limited to, sulfur, potassium, chloride, sodium, calcium, phosphorous, magnesium, zinc, iron, manganese, copper, iodine, selenium, molybdenum, cobalt, and bromine.

A "nucleotide" is an organic molecule that serves as the basic subunit of nucleic acids such as deoxyribonucleic acid (DNA) and ribonucleic acid (RNA). The term nucleotide refers to a nucleotide of any size, structure, or function. Nucleotides are typically comprised of a nitrogenous base (nucleobase), a 5- or 6-carbon sugar unit, and at least one phosphate group. Nucleotides serve as energy storage molecules in the cell, commonly in the form of nucleotide triphosphates, and are central to metabolism. The primary nucleobases are cytosine, guanine, adenine, thymine, and uracil. When a nucleobase is connected to a sugar and at least one phosphate group, the nucleotide base is formed. Common nucleotides include cytidine 5'-monophosphate (CMP), uridine 5'-monophosphate (UMP), guanosine 5'-monophosphate (GMP), and adenosine 5'-monophosphate (AMP), and salts thereof, among others.

"Lecithin" is a term used to define any fatty acid or substance that occurs naturally in a plant or animal tissue. Lecithin is a yellow-brown amphiphilic substance. In certain embodiments, lecithin may be used for smoothing food textures, dissolving powders, homogenizing liquid mixtures, repelling sticking materials, as an emulsifier, or any combination thereof. The term lecithin may also refer to any phospholipid or glycerophospholipid contained within. The term lecithin encompasses any lecithin of any size, structure, or function, and from any source. In certain embodiments, the source of lecithin is soy, soya, soybeans, eggs, milk, marine sources, rapeseed, cottonseed, sunflower, and any combination thereof. In certain embodiments, the lecithin source is soya lecithin.

"L-choline bitartrate" is a water soluble nutrient. L-choline bitartrate is a salt or monoester of choline and tartaric acid. L-choline bitartrate encompasses any salt containing the N,N,N-trimethylethanolammonium cation and complementary tartaric acid derived anion. In certain embodiments, choline bitartrate is a mixture of D/L-choline bitartrate. L-choline bitartrate contains only the L-enantiomer of choline bitartrate. In certain embodiments, L-choline bitartrate is conditioned. In certain embodiments, L-choline bitartrate is conditioned or coated with silica.

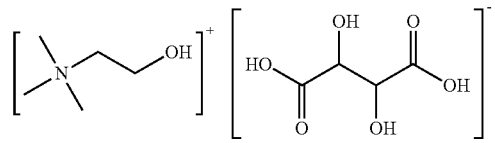

"L-carnitine" is an amino acid derivative. L-carnitine is involved in lipid and fat metabolism in mammals and other eukaryotes. The term L-carnitine encompasses any carnitine that can be classified under the IUPAC nomenclature "3-hydroxy-4-(trimethylazaniumyl)butanoate". L-carnitine can be from any food, plant, or animal source. In certain embodiments, L-carnitine is from a plant source. In certain embodiments, L-carnitine is from an animal source. L-carnitine comprises solely the biologically active L-enantiomer of carnitine.

"Beta-carotene" is a carotene, a class of terpenoids or isoprenoids. Beta-carotene is an organic pigment that has an orange or red color and is abundant in many plants and fruits. Generally, beta-carotene has about 40 carbons. The term beta-carotene also encompasses "betacarotene," "β-carotene," "Food Orange 5," "Provitamin A," "1,1'-(3,7,12,16-Tetramethyl-1,3,5,7,9,11,13,15,17-octadecanonaene-1,18-diyl)bis[2,6,6-trimethylcyclohexene]," and any carotene, terpenoid, or isoprenoid that can be classified under the IUPAC nomenclature "1,3,3-trimethyl-2-[3,7,12,16-tetramethyl-18-(2,6,6-trimethylcyclohex-1-en-1-yl) octadeca-1,3,5,7,9,11,13,15,17-nonaen-1-yl]cyclohex-1-ene." Beta-carotene can be from any food, plant, or animal source. In certain embodiments, beta-carotene is from a plant source. In certain embodiments, beta-carotene is from an animal source.

"Taurine" or "2-aminoethanesulfonic acid" is an organic compound that serves a variety of biological roles, such as conjugation of bile acids, antioxidation, osmoregulation, membrane stabilization, calcium signaling modulation, development and function of skeletal muscle, development and function of the retina, and development and function of the central nervous system. The term "taurine" encompasses any molecule that can be classified under the IUPAC nomenclature "2-aminoethanesulfonic acid." The taurine defined herein may be from any source. In certain embodiments, taurine is from an animal source.

An "effective amount" of a nutritional formula described herein refers to an amount sufficient to provide nutrition to a subject. An effective amount of a nutritional formula described herein may vary depending on such factors as the desired biological endpoint (e.g., promoting to a certain degree the postnatal development of an infant's gastrointestinal functions, nutrient absorption, immune system development), the mode of administration, and the age and health of the subject. In certain embodiments, an effective amount is a therapeutically effective amount. In certain embodiments, an effective amount is the amount of a nutritional formula described herein in a single serving. In certain embodiments, an effective amount is the amount of a nutritional formula described herein in a single feeding. In certain embodiments, an effective amount is the combined amounts of a nutritional formula described herein in multiple servings. In certain embodiments, an effective amount is the combined amounts of a nutritional formula described herein in multiple feedings.

A "therapeutically effective amount" of a nutritional formula described herein is an amount sufficient to provide a therapeutic benefit in the health (e.g., gastrointestinal development, nutritional health, nutrient absorption, immune system development, etc.), of a subject. A therapeutically effective amount of a nutritional formula means an amount of therapeutic agent, alone or in combination with other therapies, which provides a therapeutic benefit in the health of the subject. The term "therapeutically effective amount" can encompass an amount that improves overall health, reduces or avoids symptoms, signs, or causes of poor health of the subject, and/or enhances the therapeutic efficacy of another nutritional formula.

DETAILED DESCRIPTION OF CERTAIN EMBODIMENTS OF THE INVENTION

The present disclosure provides, in one aspect, a nutritional formula comprising alpha-lactalbumin enriched whey protein concentrate; beta-casein enriched milk protein; mildly hydrolyzed milk protein; lactoferrin; oleic acid-palmitic acid-oleic acid triglyceride, wherein palmitic acid is at the SN-2 position of the glycerol backbone of the triglyceride; lactose, wherein the lactose is reduced lactose; lutein; docosahexanoic acid; arachidonic acid; galactooligosaccharides; polydextrose; and combinations thereof. The invention provides for powder forms of the nutritional formula, reconstituted formulas, methods of administering the nutritional formula, and kits useful for administration of the nutritional formula to a subject. The nutritional formulas described herein are useful in providing nutrition and/or promoting postnatal development of a subject (e.g., promoting postnatal development of an infant's gastrointestinal functions, nutrient absorption, immune system development, etc.). Provided are methods of providing nutrition to (e.g., feeding) a subject in need thereof, by feeding the subject with the nutritional formulas described. Also provided are methods of providing nutrition to (e.g., feeding) a subject in need thereof, by feeding the subject with the nutritional formulas described herein reconstituted with water. Also provided are kits, methods, and uses including a nutritional formula described herein.

Nutritional Formulas and Reconstituted Formulations

In one aspect, the present disclosure provides a nutritional formula comprising:
 a) alpha-lactalbumin enriched whey protein concentrate;
 b) lactoferrin;
 c) oleic acid-palmitic acid-oleic acid triglyceride, wherein palmitic acid is at the SN-2 position of the glycerol backbone of the triglyceride;
 d) lactose, wherein the lactose is reduced lactose;
 e) lutein;
 f) docosahexanoic acid;
 g) arachidonic acid;
 h) galactooligosaccharides;
 i) polydextrose; and
 j) osteopontin.

In another aspect, the present disclosure provides a nutritional formula comprising:
 a) alpha-lactalbumin enriched whey protein concentrate;
 b) beta-casein enriched milk protein;
 c) mildly hydrolyzed milk protein;
 d) lactoferrin;
 e) oleic acid-palmitic acid-oleic acid triglyceride, wherein palmitic acid is at the SN-2 position of the glycerol backbone of the triglyceride;
 f) lactose, wherein the lactose is reduced lactose;
 g) lutein;
 h) docosahexanoic acid;
 i) arachidonic acid;
 j) galactooligosaccharides; and
 k) polydextrose.

The nutritional formula includes alpha-lactalbumin enriched whey protein concentrate. In certain embodiments, the alpha-lactalbumin enriched whey protein concentrate is sourced from a non-human animal (e.g., a cow). In certain embodiments, the alpha-lactalbumin enriched whey protein concentrate can be obtained from Arla Foods Ingredients Group. In certain embodiments, 40-60% of the whey protein concentrate is alpha-lactalbumin. In certain embodiments, approximately 40% of the whey protein concentrate is alpha-lactalbumin. In certain embodiments, approximately 43% of the whey protein concentrate is alpha-lactalbumin. In certain embodiments, approximately 46% of the whey protein concentrate is alpha-lactalbumin. In certain embodiments, approximately 50% of the whey protein concentrate is alpha-lactalbumin. In certain embodiments, approximately 60% of the whey protein concentrate is alpha-lactalbumin. In certain embodiments, the alpha-lactalbumin enriched whey protein concentrate is present in the weight range from approximately 0.25 grams to approximately 5.0 grams per liter (g/L) of reconstituted, ready-to-use reconstituted, ready-to-use nutritional formula. In certain embodiments, the alpha-lactalbumin enriched whey protein concentrate is present in the weight range from approximately 0.25 grams to approximately 4.5 grams per liter (g/L) of reconstituted, ready-to-use reconstituted, ready-to-use nutritional formula. In certain embodiments, the alpha-lactalbumin enriched whey protein concentrate is present in the weight range from approximately 0.25 grams to approximately 4.0 grams per liter (g/L) of reconstituted, ready-to-use nutritional formula. In certain embodiments, the alpha-lactalbumin enriched whey protein concentrate is present in the weight range from approximately 0.25 grams to approximately 3.5 grams per liter (g/L) of reconstituted, ready-to-use nutritional formula. In certain embodiments, the alpha-lactalbumin enriched whey protein concentrate is present in the weight range from approximately 0.25 grams to approximately 3.0 grams per liter (g/L) of reconstituted, ready-to-use nutritional formula. In certain embodiments, the alpha-lactalbumin enriched whey protein concentrate is present in the weight range from approximately 0.5 grams to approximately 3.0 grams per liter (g/L) of reconstituted, ready-to-use nutritional formula. In certain embodiments, the alpha-lactalbumin enriched whey protein concentrate is present in the weight range from approximately 0.25 grams to approximately 2.5 grams per liter (g/L) of reconstituted, ready-to-use nutritional formula. In certain embodiments, the alpha-lactalbumin enriched whey protein concentrate is present in the weight range from approximately 0.25 grams to approximately 2.0 grams per liter (g/L) of reconstituted, ready-to-use nutritional formula. In certain embodiments, the alpha-lactalbumin enriched whey protein concentrate is present in the weight range from approximately 0.25 grams to approximately 1.5 grams per liter (g/L) of reconstituted, ready-to-use nutritional formula. In certain embodiments, the alpha-lactalbumin enriched whey protein concentrate is present in the weight range from approximately 0.5 grams to approximately 1.5 grams per liter (g/L) of reconstituted, ready-to-use nutritional formula. In certain embodiments, the alpha-lactalbumin enriched whey protein concentrate is present in the weight range from approximately 0.25 grams to approximately 1.0 grams per liter (g/L) of reconstituted, ready-to-use nutritional formula. In certain embodiments, the alpha-lactalbumin enriched whey protein concentrate is present in the weight range from approximately 0.25 grams to approximately 0.5 grams per liter (g/L) of reconstituted, ready-to-use nutritional formula. In certain embodiments, the alpha-lactalbumin enriched whey protein concentrate is present in the weight range from approximately 2.5 grams to approximately 3.0 grams per liter (g/L) of reconstituted, ready-to-use nutritional formula. In certain embodiments, the nutritional formula includes approximately 2.8 grams of alpha-lactalbumin enriched whey protein concentrate per liter (g/L) of reconstituted, ready-to-use nutritional formula. In certain embodiments, the nutritional formula includes approximately 2.715 grams of alpha-lactalbumin enriched whey protein concentrate per liter (g/L) of reconstituted, ready-to-use nutritional formula. In certain embodiments, the nutritional formula includes approximately 2.7 grams of alpha-lactalbumin enriched whey protein concentrate per liter (g/L) of reconstituted, ready-to-use nutritional formula. In certain embodiments, the nutritional formula includes approximately 1.4 grams of alpha-lactalbumin enriched whey protein concentrate per liter (g/L) of reconstituted, ready-to-use nutritional formula. In certain embodiments, the nutritional formula includes approximately 1.385 grams of alpha-lactalbumin enriched whey protein concentrate per liter (g/L) of reconstituted, ready-to-use nutritional formula. In certain embodiments, the nutritional formula includes approximately 1.3 grams of alpha-lactalbumin enriched whey protein concentrate per liter (g/L) of reconstituted, ready-to-use nutritional formula.

The nutritional formula includes alpha-lactalbumin. The alpha-lactalbumin may be obtained from any source. In certain embodiments, the source of alpha-lactalbumin is demineralized whey, whey protein concentrate, skimmed milk powder, alpha-lactalbumin enriched whey protein concentrate, or combinations thereof. In certain embodiments, the alpha-lactalbumin is present in the weight range of 0.25 grams to approximately 5.0 grams per liter (g/L) of reconstituted, ready-to-use reconstituted, ready-to-use nutritional formula. In certain embodiments, the alpha-lactalbumin is present in the weight range from approximately 0.25 grams to approximately 4.5 grams per liter (g/L) of reconstituted, ready-to-use reconstituted, ready-to-use nutritional formula. In certain embodiments, the alpha-lactalbumin is present in the weight range from approximately 0.25 grams to approximately 4.0 grams per liter (g/L) of reconstituted, ready-to-use nutritional formula. In certain embodiments, the alpha-lactalbumin is present in the weight range from approximately 3.25 grams to approximately 3.75 grams per liter (g/L) of reconstituted, ready-to-use nutritional formula. In certain embodiments, the alpha-lactalbumin is present in the weight range from approximately 0.25 grams to approximately 3.5 grams per liter (g/L) of reconstituted, ready-to-use nutritional formula. In certain embodiments, the alpha-lactalbumin is present in the weight range from approximately 0.25 grams to approximately 3.0 grams per liter (g/L) of reconstituted, ready-to-use nutritional formula. In certain embodiments, the alpha-lactalbumin is present in the weight range from approximately 0.5 grams to approximately 3.0 grams per liter (g/L) of reconstituted, ready-to-use nutritional formula. In certain embodiments, the alpha-lactalbumin is present in the weight range from approximately 0.25 grams to approximately 2.5 grams per liter (g/L) of reconstituted, ready-to-use nutritional formula. In certain embodiments, the alpha-lactalbumin is present in the weight range from approximately 0.25 grams to approximately 2.0 grams per liter (g/L) of reconstituted, ready-to-use nutritional formula. In certain embodiments, the alpha-lactalbumin is present in the weight range from approximately 0.25 grams to approximately 1.5 grams per liter (g/L) of reconstituted, ready-to-use nutritional formula. In certain embodiments, the alpha-lactalbumin is present in the weight range from approximately 0.5 grams to approximately 1.5 grams per liter (g/L) of reconstituted, ready-to-use nutritional formula. In certain embodiments, the alpha-lactalbumin is present in the weight range from approximately 0.25 grams to approximately 1.0 grams per liter (g/L) of reconstituted, ready-to-use nutritional formula. In certain embodiments, the alpha-lactalbumin is present in the weight range from approximately 0.25 grams to approximately 0.5 grams per liter (g/L) of reconstituted, ready-to-use nutritional formula. In certain embodiments, the nutritional formula includes approximately 2.7 grams of alpha-lactalbumin per liter (g/L) of reconstituted, ready-to-use nutritional formula. In certain embodiments, the nutritional formula includes approximately 2.661 grams of alpha-lactalbumin enriched whey protein concentrate per liter (g/L) of reconstituted, ready-to-use nutritional formula. In certain embodiments, the nutritional formula includes approximately 2.6 grams of alpha-lactalbumin enriched whey protein concentrate per liter (g/L) of reconstituted, ready-to-use nutritional formula. In certain embodiments, the nutritional formula includes approximately 2.577 grams of alpha-lactalbumin enriched whey protein concentrate per liter (g/L) of reconstituted, ready-to-use nutritional formula. In certain embodiments, the nutritional formula includes approximately 2.5 grams of alpha-lactalbumin enriched whey protein concentrate per liter (g/L) of reconstituted, ready-to-use nutritional formula. In certain embodiments, the nutritional formula includes approximately 3.6 grams of alpha-lactalbumin per liter (g/L) of reconstituted, ready-to-use nutritional formula. In certain embodiments, the nutritional formula includes approximately 3.592 grams of alpha-lactalbumin enriched whey protein concentrate per liter (g/L) of reconstituted, ready-to-use nutritional formula. In certain embodiments, the nutritional formula includes approximately 3.5 grams of alpha-lactalbumin enriched whey protein concentrate per liter (g/L) of reconstituted, ready-to-use nutritional formula. In certain embodiments, the nutritional formula includes approximately 3.479 grams of alpha-lactalbumin enriched whey protein concentrate per liter (g/L) of reconstituted, ready-to-use nutritional formula. In certain embodiments, the nutritional formula includes approximately 3.4 grams of alpha-lactalbumin enriched whey protein concentrate per liter (g/L) of reconstituted, ready-to-use nutritional formula.

The nutritional formula includes osteopontin. In certain embodiments, the osteopontin is derived from milk. The milk for osteopontin production may be obtained from any source. In certain embodiments, the osteopontin is sourced from a non-human animal (e.g., a cow). In certain embodiments, the osteopontin can be obtained from Arla Foods. In certain embodiments, the osteopontin is present in the weight range from approximately 0.01 grams to approximately 1.5 grams per liter (g/L) of reconstituted, ready-to-use nutritional formula. In certain embodiments, the osteopontin is present in the weight range from approximately 0.1 grams to approximately 1.5 grams per liter (g/L) of reconstituted, ready-to-use nutritional formula. In certain embodiments, the osteopontin is present in the weight range from approximately 0.01 grams to approximately 1.0 grams per liter (g/L) of reconstituted, ready-to-use nutritional formula. In certain embodiments, the osteopontin is present in the weight range from approximately 0.1 grams to approximately 1.0 grams per liter (g/L) of reconstituted, ready-to-use nutritional formula. In certain embodiments, the osteopontin is present in the weight range from approximately 0.01 grams to approximately 0.5 grams per liter (g/L) of reconstituted, ready-to-use nutritional formula. In certain embodiments, the osteopontin is present in the weight range from approximately 0.1 grams to approximately 0.5 grams per liter (g/L) of reconstituted, ready-to-use nutritional formula. In certain embodiments, the osteopontin is present in the weight range from approximately 0.01 grams to approximately 0.25 grams per liter (g/L) of reconstituted, ready-to-use nutritional formula. In certain embodiments, the osteopontin is present in the weight range from approximately 0.1 grams to approximately 0.25 grams per liter (g/L) of reconstituted, ready-to-use nutritional formula. In certain embodiments, the osteopontin is present in the weight range from approximately 0.01 grams to approximately 0.15 grams per liter (g/L) of reconstituted, ready-to-use nutritional formula. In certain embodiments, the osteopontin is present in the weight range from approximately 0.1 grams to approximately 0.15 grams per liter (g/L) of reconstituted, ready-to-use nutritional formula. In certain embodiments, the osteopontin is present in the weight range from approximately 0.01 grams to approximately 0.1 grams per liter (g/L) of reconstituted, ready-to-use nutritional formula. In certain embodiments, the osteopontin is present in the weight range from approximately 0.01 grams to approximately 0.05 grams per liter (g/L) of reconstituted, ready-to-use nutritional formula. In certain embodiments, the nutritional formula includes approximately 0.17 grams of osteopontin per liter (g/L) of reconstituted, ready-to-use nutritional formula. In certain embodiments, the nutritional formula includes approximately 0.163 grams of osteopontin per liter (g/L) of reconstituted, ready-to-use nutritional formula. In certain embodiments, the nutritional formula includes approximately 0.16 grams of osteopontin per liter (g/L) of reconstituted, ready-to-use nutritional formula. In certain embodiments, the osteopontin is Lacprodan® OPN-10. In certain embodiments, Lacprodan® OPN-10 is obtained from Arla Foods.

The nutritional formula includes skimmed milk powder. In certain embodiments, the skimmed milk powder is produced from skimmed milk protein. In certain embodiments, the skimmed milk protein is sourced from a non-human animal (e.g., a cow). In certain embodiments, 0.1-5% of the skimmed milk powder is moisture by weight. In certain embodiments, 5% or less of the skimmed milk powder is moisture by weight. In certain embodiments, 0.1-1.5% of the skimmed milk powder is milkfat by weight. In certain embodiments, 1.5% or less of the skimmed milk powder is milkfat by weight. In certain embodiments, 34-60% of the skimmed milk powder is milk protein. In certain embodiments, 34% or more of the skimmed milk powder is milk protein. In certain embodiments, the skimmed milk powder is present in the weight range from approximately 5 grams to approximately 50 grams per liter (g/L) of reconstituted, ready-to-use nutritional formula. In certain embodiments, the skimmed milk powder is present in the weight range from approximately 5 grams to approximately 45 grams per liter (g/L) of reconstituted, ready-to-use nutritional formula. In certain embodiments, the skimmed milk powder is present in the weight range from approximately 5 grams to approximately 40 grams per liter (g/L) of reconstituted, ready-to-use nutritional formula. In certain embodiments, the skimmed milk powder is present in the weight range from approximately 10 grams to approximately 40 grams per liter (g/L) of reconstituted, ready-to-use nutritional formula. In certain embodiments, the skimmed milk powder is present in the weight range from approximately 5 grams to approximately 35 grams per liter (g/L) of reconstituted, ready-to-use nutritional formula. In certain embodiments, the skimmed milk powder is present in the weight range from approximately 5 grams to approximately 30 grams per liter (g/L) of reconstituted, ready-to-use nutritional formula. In certain embodiments, the skimmed milk powder is present in the weight range from approximately 10 grams to approximately 30 grams per liter (g/L) of reconstituted, ready-to-use nutritional formula. In certain embodiments, the skimmed milk powder is present in the weight range from approximately 5 grams to approximately 25 grams per liter (g/L) of reconstituted, ready-to-use nutritional formula. In certain embodiments, the skimmed milk powder is present in the weight range from approximately 5 grams to approximately 20 grams per liter (g/L) of reconstituted, ready-to-use nutritional formula. In certain embodiments, the skimmed milk powder is present in the weight range from approximately 10 grams to approximately 20 grams per liter (g/L) of reconstituted, ready-to-use nutritional formula. In certain embodiments, the skimmed milk powder is present in the weight range from approximately 5 grams to approximately 15 grams per liter (g/L) of reconstituted, ready-to-use nutritional formula. In certain embodiments, the skimmed milk powder is present in the weight range from approximately 5 grams to approximately 10 grams per liter (g/L) of reconstituted, ready-to-use nutritional formula. In certain embodiments, the nutritional formula includes approximately 17 grams of skimmed milk powder per liter (g/L) of reconstituted, ready-to-use nutritional formula. In certain embodiments, the nutritional formula includes approximately 16.780 grams of skimmed milk powder per liter (g/L) of reconstituted, ready-to-use nutritional formula. In certain embodiments, the nutritional formula includes approximately 16 grams of skimmed milk powder per liter (g/L) of reconstituted, ready-to-use nutritional formula.

In certain embodiments, the nutritional formula includes beta-casein enriched milk protein. In certain embodiments, the beta-casein enriched milk protein is sourced from a non-human animal (e.g., a cow). In certain embodiments, the beta-casein enriched milk protein can be obtained from IOI Loders Croklaan, Loders Croklaan B.V., and/or Kerry. In certain embodiments, 30-60% of the milk protein fraction is beta-casein. In certain embodiments, approximately 30% of the milk protein fraction is beta-casein. In certain embodiments, approximately 40% of the milk protein fraction is beta-casein. In certain embodiments, approximately 50% of the milk protein fraction is beta-casein. In certain embodiments, approximately 60% of the milk protein fraction is beta-casein. In certain embodiments, the beta-casein enriched milk protein is present in the weight range from approximately 0.25 grams to approximately 5.0 grams per liter (g/L) of reconstituted, ready-to-use nutritional formula. In certain embodiments, the beta-casein enriched milk protein is present in the weight range from approximately 0.25 grams to approximately 4.5 grams per liter (g/L) of reconstituted, ready-to-use nutritional formula. In certain embodiments, the beta-casein enriched milk protein is present in the weight range from approximately 0.25 grams to approximately 4.0 grams per liter (g/L) of reconstituted, ready-to-use nutritional formula. In certain embodiments, the beta-casein enriched milk protein is present in the weight range from approximately 0.25 grams to approximately 3.5 grams per liter (g/L) of reconstituted, ready-to-use nutritional formula. In certain embodiments, the beta-casein enriched milk protein is present in the weight range from approximately 0.25 grams to approximately 3.0 grams per liter (g/L) of reconstituted, ready-to-use nutritional formula. In certain embodiments, the beta-casein enriched milk protein is present in the weight range from approximately 0.5 grams to approximately 3.0 grams per liter (g/L) of reconstituted, ready-to-use nutritional formula. In certain embodiments, the beta-casein enriched milk protein is present in the weight range from approximately 0.25 grams to approximately 2.5 grams per liter (g/L) of reconstituted, ready-to-use nutritional formula. In certain embodiments, the beta-casein enriched milk protein is present in the weight range from approximately 0.25 grams to approximately 2.0 grams per liter (g/L) of reconstituted, ready-to-use nutritional formula. In certain embodiments, the beta-casein enriched milk protein is present in the weight range from approximately 0.25 grams to approximately 1.5 grams per liter (g/L) of reconstituted, ready-to-use nutritional formula. In certain embodiments, the beta-casein enriched milk protein is present in the weight range from approximately 0.5 grams to approximately 1.5 grams per liter (g/L) of reconstituted, ready-to-use nutritional formula. In certain embodiments, the beta-casein enriched milk protein is present in the weight range from approximately 0.25 grams to approximately 1.0 grams per liter (g/L) of reconstituted, ready-to-use nutritional formula. In certain embodiments, the beta-casein enriched milk protein is present in the weight range from approximately 0.25 grams to approximately 0.5 grams per liter (g/L) of reconstituted, ready-to-use nutritional formula. In certain embodiments, the nutritional formula includes approximately 1.4 grams of beta-casein enriched milk protein per liter (g/L) of reconstituted, ready-to-use nutritional formula. In certain embodiments, the nutritional formula includes approximately 1.385 grams of beta-casein enriched milk protein per liter (g/L) of reconstituted, ready-to-use nutritional formula. In certain embodiments, the nutritional formula includes approximately 1.3 grams of beta-casein enriched milk protein per liter (g/L) of reconstituted, ready-to-use nutritional formula.

In certain embodiments, the nutritional formula includes mildly hydrolyzed milk protein. In certain embodiments, the mildly hydrolyzed milk protein is present in the weight range of approximately 5 grams to approximately 50 grams per liter (g/L) of reconstituted, ready-to-use nutritional formula. In certain embodiments, the mildly hydrolyzed milk protein is present in the weight range of approximately 5 grams to approximately 45 grams per liter (g/L) of reconstituted, ready-to-use nutritional formula. In certain embodiments, the mildly hydrolyzed milk protein is present in the weight range of approximately 5 grams to approximately 40 grams per liter (g/L) of reconstituted, ready-to-use nutritional formula. In certain embodiments, the mildly hydrolyzed milk protein is present in the weight range from approximately 10 grams to approximately 40 grams per liter (g/L) of reconstituted, ready-to-use nutritional formula. In certain embodiments, the mildly hydrolyzed milk protein is present in the weight range of approximately 5 grams to approximately 35 grams per liter (g/L) of reconstituted, ready-to-use nutritional formula. In certain embodiments, the mildly hydrolyzed milk protein is present in the weight range of approximately 5 grams to approximately 30 grams per liter (g/L) of reconstituted, ready-to-use nutritional formula. In certain embodiments, the mildly hydrolyzed milk protein is present in the weight range from approximately 10 grams to approximately 30 grams per liter (g/L) of reconstituted, ready-to-use nutritional formula. In certain embodiments, the mildly hydrolyzed milk protein is present in the weight range of approximately 5 grams to approximately 25 grams per liter (g/L) of reconstituted, ready-to-use nutritional formula. In certain embodiments, the mildly hydrolyzed milk protein is present in the weight range of approximately 5 grams to approximately 20 grams per liter (g/L) of reconstituted, ready-to-use nutritional formula. In certain embodiments, the mildly hydrolyzed milk protein is present in the weight range of approximately 5 grams to approximately 15 grams per liter (g/L) of reconstituted, ready-to-use nutritional formula. In certain embodiments, the mildly hydrolyzed milk protein is present in the weight range of approximately 5 grams to approximately 10 grams per liter (g/L) of reconstituted, ready-to-use nutritional formula. In certain embodiments, the nutritional formula includes approximately 28.0 grams of mildly hydrolyzed milk protein per liter (g/L) of reconstituted, ready-to-use nutritional formula. In certain embodiments, the nutritional formula includes approximately 27.983 grams of mildly hydrolyzed milk protein per liter (g/L) of reconstituted, ready-to-use nutritional formula. In certain embodiments, the nutritional formula includes approximately 27.0 grams of mildly hydrolyzed milk protein per liter (g/L) of reconstituted, ready-to-use nutritional formula.

The nutritional formula includes lactoferrin. In certain embodiments, the lactoferrin is from a non-human animal (e.g., a cow). In certain embodiments, the lactoferrin can be obtained from IOI Loders Croklaan, Loders Croklaan B.V., Milei GmbH and/or Kerry. In certain embodiments, lactoferrin is present in the weight range of approximately 0.01 grams to approximately 1.5 grams per liter (g/L) of reconstituted, ready-to-use nutritional formula. In certain embodiments, lactoferrin is present in the weight range of approximately 0.01 grams to approximately 1.0 grams per liter (g/L) of reconstituted, ready-to-use nutritional formula. In certain embodiments, the lactoferrin is present in the weight range from approximately 0.05 grams to approximately 1.0 grams per liter (g/L) of reconstituted, ready-to-use nutritional formula. In certain embodiments, lactoferrin is present in the weight range of approximately 0.01 grams to approximately 0.5 grams per liter (g/L) of reconstituted, ready-to-use nutritional formula. In certain embodiments, the lactoferrin is present in the weight range from approximately 0.05 grams to approximately 0.2 grams per liter (g/L) of reconstituted, ready-to-use nutritional formula. In certain embodiments, lactoferrin is present in the weight range of approximately 0.01 grams to approximately 0.1 grams per liter (g/L) of reconstituted, ready-to-use nutritional formula. In certain embodiments, lactoferrin is present in the weight range of approximately 0.01 grams to approximately 0.05 grams per liter (g/L) of reconstituted, ready-to-use nutritional formula. In certain embodiments, the nutritional formula includes approximately 0.14 grams of lactoferrin per liter (g/L) of reconstituted, ready-to-use nutritional formula. In certain embodiments, the nutritional formula includes approximately 0.135 grams of lactoferrin per liter (g/L) of reconstituted, ready-to-use nutritional formula. In certain embodiments, the nutritional formula includes approximately 0.13 grams of lactoferrin per liter (g/L) of reconstituted, ready-to-use nutritional formula. In certain embodiments, the nutritional formula includes approximately 0.07 grams of lactoferrin per liter (g/L) of reconstituted, ready-to-use nutritional formula. In certain embodiments, the nutritional formula includes approximately 0.064 grams of lactoferrin per liter (g/L) of reconstituted, ready-to-use nutritional formula. In certain embodiments, the nutritional formula includes approximately 0.06 grams of lactoferrin per liter (g/L) of reconstituted, ready-to-use nutritional formula. In certain embodiments, the lactoferrin is MLF-2M. In certain embodiments, MLF-2M is obtained from Milei GmbH.

In one aspect, the present nutritional formula includes a vegetable oil blend. In certain embodiments, the vegetable oil blend includes soybean oil, soya lecithin, coconut oil, or combinations thereof. In certain embodiments, the vegetable oil blend includes soybean oil. In certain embodiments, the vegetable oil blend includes soya lecithin. In certain embodiments, the vegetable oil blend includes coconut oil. In certain embodiments, the vegetable oil blend includes oleic acid-palmitic acid-oleic acid triglyceride, wherein palmitic acid is at the SN-2 position of the glycerol backbone of the triglyceride. In certain embodiments, the oleic acid-palmitic acid-oleic acid triglyceride is of Formula (I):

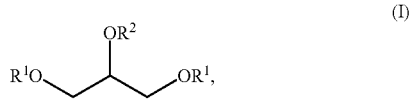

(I)

wherein $R^1$ is oleic acid (C18:1), and $R^2$ is palmitic acid (C16:0). In certain embodiments, the SN-2 position of the glycerol backbone of the triglyceride is the second position on the glycerol backbone of the triglyceride. In certain embodiments, the oleic acid-palmitic acid-oleic acid triglyceride is vegetable-derived. In certain embodiments, the oleic acid-palmitic acid-oleic acid triglyceride is from high oleic sunflower oil, palm oil, or combinations thereof. In certain embodiments, the oleic acid-palmitic acid-oleic acid triglyceride is from sunflower oil. In certain embodiments, the oleic acid-palmitic acid-oleic acid triglyceride is from high oleic sunflower oil. In certain embodiments, the oleic acid-palmitic acid-oleic acid triglyceride is from palm oil. In certain embodiments, the vegetable oil blend comprising oleic acid-palmitic acid-oleic acid triglyceride is Betapol DP9100. Betapol DP9100 can be obtained from IOI Loders Croklaan, Loders Croklaan B.V., and/or Kerry.

In certain embodiments, the nutritional formula includes the vegetable oil blend in the following weight range, in grams per liter (g/L) of reconstituted, ready-to-use nutritional formula: approximately 20 grams to approximately 45 grams of the vegetable oil blend per L of reconstituted, ready-to-use nutritional formula. In certain embodiments, the nutritional formula includes approximately 25 grams to approximately 40 grams of the vegetable oil blend per L of reconstituted, ready-to-use nutritional formula. In certain embodiments, the nutritional formula includes approximately 30 grams to approximately 40 grams of the vegetable oil blend per L of reconstituted, ready-to-use nutritional formula. In certain embodiments, the nutritional formula includes approximately 35 grams to approximately 40 grams of the vegetable oil blend per L of reconstituted, ready-to-use nutritional formula. In certain embodiments, the nutritional formula includes approximately 37 grams of the vegetable oil blend per L of reconstituted, ready-to-use nutritional formula. In certain embodiments, the nutritional formula includes approximately 36.519 grams of the vegetable oil blend per L of reconstituted, ready-to-use nutritional formula. In certain embodiments, the nutritional formula includes approximately 36 grams of the vegetable oil blend per L of reconstituted, ready-to-use nutritional formula. In certain embodiments, the nutritional formula includes approximately 35 grams of the vegetable oil blend per L of reconstituted, ready-to-use nutritional formula.

The nutritional formula includes the oleic acid-palmitic acid-oleic acid triglyceride in the following weight range, in grams per liter (g/L) of reconstituted, ready-to-use nutritional formula: approximately 0.1 grams to approximately 1.5 grams of the oleic acid-palmitic acid-oleic acid triglyceride per L of reconstituted, ready-to-use nutritional formula. In certain embodiments, the nutritional formula includes approximately 0.1 grams to approximately 1.25 grams of the oleic acid-palmitic acid-oleic acid triglyceride per L of reconstituted, ready-to-use nutritional formula. In certain embodiments, the nutritional formula includes approximately 0.1 grams to approximately 1.0 grams of the oleic acid-palmitic acid-oleic acid triglyceride per L of reconstituted, ready-to-use nutritional formula. In certain embodiments, the nutritional formula includes approximately 0.1 grams to approximately 0.75 grams of the oleic acid-palmitic acid-oleic acid triglyceride per L of reconstituted, ready-to-use nutritional formula. In certain embodiments, the nutritional formula includes approximately 0.3 grams to approximately 0.6 grams of the oleic acid-palmitic acid-oleic acid triglyceride per L of reconstituted, ready-to-use nutritional formula. In certain embodiments, the nutritional formula includes approximately 0.4 grams to approximately 0.6 grams of the oleic acid-palmitic acid-oleic acid triglyceride per L of reconstituted, ready-to-use nutritional formula. In certain embodiments, the nutritional formula includes approximately 0.6 grams of the oleic acid-palmitic acid-oleic acid triglyceride per L of reconstituted, ready-to-use nutritional formula. In certain embodiments, the nutritional formula includes approximately 0.5 grams of the oleic acid-palmitic acid-oleic acid triglyceride per L of reconstituted, ready-to-use nutritional formula. In certain embodiments, the nutritional formula includes the oleic acid-palmitic acid-oleic acid triglyceride in the following weight range, in grams per liter (g/L) of reconstituted, ready-to-use nutritional formula: approximately 0.5 grams to approximately 5.0 grams of the oleic acid-palmitic acid-oleic acid triglyceride per L of reconstituted, ready-to-use nutritional formula. In certain embodiments, the nutritional formula includes approximately 0.5 grams to approximately 4.5 grams of the oleic acid-palmitic acid-oleic acid triglyceride per L of reconstituted, ready-to-use nutritional formula. In certain embodiments, the nutritional formula includes approximately 0.5 grams to approximately 4.0 grams of the oleic acid-palmitic acid-oleic acid triglyceride per L of reconstituted, ready-to-use nutritional formula. In certain embodiments, the nutritional formula includes approximately 0.5 grams to approximately 3.5 grams of the oleic acid-palmitic acid-oleic acid triglyceride per L of reconstituted, ready-to-use nutritional formula. In certain embodiments, the nutritional formula includes approximately 0.5 grams to approximately 3.0 grams of the oleic acid-palmitic acid-oleic acid triglyceride per L of reconstituted, ready-to-use nutritional formula. In certain embodiments, the nutritional formula includes approximately 0.5 grams to approximately 2.5 grams of the oleic acid-palmitic acid-oleic acid triglyceride per L of reconstituted, ready-to-use nutritional formula. In certain embodiments, the nutritional formula includes approximately 0.5 grams to approximately 2.0 grams of the oleic acid-palmitic acid-oleic acid triglyceride per L of reconstituted, ready-to-use nutritional formula. In certain embodiments, the nutritional formula includes approximately 0.5 grams to approximately 1.5 grams of the oleic acid-palmitic acid-oleic acid triglyceride per L of reconstituted, ready-to-use nutritional formula. In certain embodiments, the nutritional formula includes approximately 0.5 grams to approximately 1.0 grams of the oleic acid-palmitic acid-oleic acid triglyceride per L of reconstituted, ready-to-use nutritional formula. In certain embodiments, the nutritional formula includes approximately 5.0 grams of the oleic acid-palmitic acid-oleic acid triglyceride per L of reconstituted, ready-to-use nutritional formula. In certain embodiments, the nutritional formula includes approximately 4.5 grams of the oleic acid-palmitic acid-oleic acid triglyceride per L of reconstituted, ready-to-use nutritional formula. In certain embodiments, the nutritional formula includes approximately 4.0 grams of the oleic acid-palmitic acid-oleic acid triglyceride per L of reconstituted, ready-to-use nutritional formula.

The present nutritional formula includes carbohydrates. In certain embodiments, the carbohydrates include lactose. In certain embodiments, the lactose is reduced lactose. In certain embodiments, the nutritional formula includes the following weight range of lactose, in grams per liter (g/L) of reconstituted, ready-to-use nutritional formula: approximately 0.5 grams to approximately 3.0 grams of lactose per L of reconstituted, ready-to-use nutritional formula. In certain embodiments, the nutritional formula includes approximately 0.5 grams to approximately 2.5 grams of lactose per L of reconstituted, ready-to-use nutritional formula. In certain embodiments, the nutritional formula includes approximately 0.5 grams to approximately 2.0 grams of lactose per L of reconstituted, ready-to-use nutritional formula. In certain embodiments, the nutritional formula includes approximately 0.5 grams to approximately 1.75 grams of lactose per L of reconstituted, ready-to-use nutritional formula. In certain embodiments, the nutritional formula includes approximately 1.0 grams to approximately 1.75 grams of lactose per L of reconstituted, ready-to-use nutritional formula. In certain embodiments, the nutritional formula includes approximately 1.5 grams to approximately 1.75 grams of lactose per L of reconstituted, ready-to-use nutritional formula. In certain embodiments, the nutritional formula includes approximately 1.7 grams of lactose per L of reconstituted, ready-to-use nutritional formula. In certain embodiments, the nutritional formula includes approximately 1.6 grams of lactose per L of reconstituted, ready-to-use nutritional formula. In certain embodiments, the carbohydrates include maltodextrin. In certain embodiments, the nutritional formula includes the following weight range of lactose, in grams per liter (g/L) of reconstituted, ready-to-use nutritional formula: approximately 30 grams to approximately 50 grams of lactose per L of reconstituted, ready-to-use nutritional formula. In certain embodiments, the nutritional formula includes approximately 40 grams to approximately 50 grams of lactose per L of reconstituted, ready-to-use nutritional formula. In certain embodiments, the nutritional formula includes approximately 30 grams to approximately 45 grams of lactose per L of reconstituted, ready-to-use nutritional formula. In certain embodiments, the nutritional formula includes approximately 35 grams to approximately 45 grams of lactose per L of reconstituted, ready-to-use nutritional formula. In certain embodiments, the nutritional formula includes approximately 40 grams to approximately 45 grams of lactose per L of reconstituted, ready-to-use nutritional formula. In certain embodiments, the nutritional formula includes approximately 30 grams to approximately 40 grams of lactose per L of reconstituted, ready-to-use nutritional formula. In certain embodiments, the nutritional formula includes approximately 30 grams to approximately 35 grams of lactose per L of reconstituted, ready-to-use nutritional formula. In certain embodiments, the nutritional formula includes approximately 42 grams of lactose per L of reconstituted, ready-to-use nutritional formula. In certain embodiments, the nutritional formula includes approximately 41.814 grams of lactose per L of reconstituted, ready-to-use nutritional formula. In certain embodiments, the nutritional formula includes approximately 41 grams of lactose per L of reconstituted, ready-to-use nutritional formula. In certain embodiments, the nutritional formula includes approximately 40.582 grams of lactose per L of reconstituted, ready-to-use nutritional formula. In certain embodiments, the nutritional formula includes approximately 40 grams of lactose per L of reconstituted, ready-to-use nutritional formula. In certain embodiments, the nutritional formula includes approximately 50 to 75 grams of maltodextrin per L of reconstituted, ready-to-use nutritional formula. In certain embodiments, the nutritional formula includes approximately 60 grams of maltodextrin per L of reconstituted, ready-to-use nutritional formula. In certain embodiments, the nutritional formula includes approximately 57 grams of maltodextrin per L of reconstituted, ready-to-use nutritional formula.

In certain embodiments, the nutritional formula includes one or more antioxidants. In certain embodiments, the antioxidants include lutein. In certain embodiments, the nutritional formula includes lutein. In certain embodiments, the nutritional formula includes the following weight range of lutein, in grams per liter (g/L) of reconstituted, ready-to-use nutritional formula: approximately 0.0025 grams to approximately 0.05 grams of lutein per L of reconstituted, ready-to-use nutritional formula. In certain embodiments, the nutritional formula includes approximately 0.0025 grams to approximately 0.025 grams of lutein per L of reconstituted, ready-to-use nutritional formula. In certain embodiments, the nutritional formula includes approximately 0.020 grams to approximately 0.025 grams of lutein per L of reconstituted, ready-to-use nutritional formula. In certain embodiments, the nutritional formula includes approximately 0.021 grams of lutein per L of reconstituted, ready-to-use nutritional formula. In certain embodiments, the nutritional formula includes approximately 0.0206 grams of lutein per L of reconstituted, ready-to-use nutritional formula.

In certain embodiments, the nutritional formula includes polyunsaturated fatty acids. In certain embodiments, the polyunsaturated fatty acids include docosahexanoic acid, arachidonic acid, linoleic acid, alpha-linolenic acid, or combinations thereof. In certain embodiments, the nutritional formula includes docosahexanoic acid, arachidonic acid, linoleic acid, and alpha-linolenic acid. In certain embodiments, the nutritional formula includes docosahexanoic acid and arachidonic acid. In certain embodiments, the nutritional formula includes *Crypthecodinium cohnii* oil, fish oil, or combinations, or powders thereof. In certain embodiments, the nutritional formula includes *Crypthecodinium cohnii* oil in powdered form. In certain embodiments, the *Crypthecodinium cohnii* oil powder is between 15-20% docosahexanoic acid. In certain embodiments, the *Crypthecodinium cohnii* oil powder is between 15-18% docosahexanoic acid. In certain embodiments, the *Crypthecodinium cohnii* oil powder is approximately 19% docosahexanoic acid. In certain embodiments, the docosahexanoic acid is from *Crypthecodinium cohnii* oil, fish oil, or combinations thereof. In certain embodiments, the docosahexanoic acid is from Driphorm® SCO DHA 50. In certain embodiments, the docosahexanoic acid is sourced from Martek Biosciences Corporation, NuMega Ingredients, DSM Nutritional Products, and/or Royal DSM. In certain embodiments, the docosahexanoic acid is from *Crypthecodinium cohnii* oil. In certain embodiments, the docosahexanoic acid is from fish oil. In certain embodiments, the docosahexanoic acid is from *Crypthecodinium cohnii* oil and fish oil. In certain embodiments, the docosahexanoic acid is microencapsulated. In certain embodiments, the arachidonic acid is microencapsulated. In certain embodiments, the docosahexanoic acid and arachidonic acid are both microencapsulated.

In certain embodiments, the nutritional formula includes the following weight range of docosahexanoic acid and arachidonic acid, in grams per liter (g/L) of reconstituted, ready-to-use nutritional formula: approximately 0.25 grams to approximately 1.5 grams of a combination of docosahexanoic acid and arachidonic acid per L of reconstituted, ready-to-use nutritional formula. In certain embodiments, the nutritional formula includes approximately 0.2 grams to approximately 1.5 grams of a combination of docosahexanoic acid and arachidonic acid per L of reconstituted, ready-to-use nutritional formula. In certain embodiments, the nutritional formula includes approximately 0.5 grams to approximately 1.0 grams of a combination of docosahexanoic acid and arachidonic acid per L of reconstituted, ready-to-use nutritional formula. In certain embodiments, the nutritional formula includes approximately 1.296 grams of a combination of docosahexanoic acid and arachidonic acid per L of reconstituted, ready-to-use nutritional formula. In certain embodiments, the nutritional formula includes docosahexanoic acid. In certain embodiments, the nutritional formula includes approximately 0.01 grams to approximately 0.10 grams of docosahexanoic acid per L of reconstituted, ready-to-use nutritional formula. In certain embodiments, the nutritional formula includes approximately 0.05 grams to approximately 0.09 grams of docosahexanoic acid per L of reconstituted, ready-to-use nutritional formula. In certain embodiments, the nutritional formula includes approximately 0.05 grams to approximately 0.085 grams of docosahexanoic acid per L of reconstituted, ready-to-use nutritional formula. In certain embodiments, the nutritional formula includes approximately 0.05 grams to approximately 0.09 grams of docosahexanoic acid per L of reconstituted, ready-to-use nutritional formula. In certain embodiments, the nutritional formula includes approximately 0.01 grams to approximately 0.083 grams of docosahexanoic acid per L of reconstituted, ready-to-use nutritional formula. In certain embodiments, the nutritional formula includes approximately 0.06 grams to approximately 0.083 grams of docosahexanoic acid per L of reconstituted, ready-to-use nutritional formula. In certain embodiments, the nutritional formula includes approximately 0.083 grams of docosahexanoic acid per L of reconstituted, ready-to-use nutritional formula. In certain embodiments, the nutritional formula includes approximately 0.070 grams of docosahexanoic acid per L of reconstituted, ready-to-use nutritional formula. In certain embodiments, the nutritional formula includes approximately 0.67 grams of docosahexanoic acid per L of reconstituted, ready-to-use nutritional formula. In certain embodiments, the nutritional formula includes approximately 0.060 grams of docosahexanoic acid per L of reconstituted, ready-to-use nutritional formula.

In certain embodiments, the nutritional formula includes *Mortierella alpina* oil. In certain embodiments, the arachidonic acid is from *Mortierella alpina* oil. In certain embodiments, the nutritional formula includes arachidonic acid. In certain embodiments, the arachidonic acid is sourced from Martek Biosciences Corporation, NuMega Ingredients, DSM Nutritional Products, and/or Royal DSM. In certain embodiments, the nutritional formula includes approximately 0.1 grams to approximately 1.0 grams of arachidonic acid per L of reconstituted, ready-to-use nutritional formula. In certain embodiments, the nutritional formula includes approximately 0.5 grams to approximately 1.0 grams of arachidonic acid per L of reconstituted, ready-to-use nutritional formula. In certain embodiments, the nutritional formula includes approximately 0.75 grams to approximately 1.0 grams of arachidonic acid per L of reconstituted, ready-to-use nutritional formula. In certain embodiments, the nutritional formula includes approximately 0.9 grams of arachidonic acid per L of reconstituted, ready-to-use nutritional formula. In certain embodiments, the nutritional formula includes approximately 0.86 grams of arachidonic acid per L of reconstituted, ready-to-use nutritional formula. In certain embodiments, the nutritional formula includes approximately 0.8 grams of arachidonic acid per L of reconstituted, ready-to-use nutritional formula. In certain embodiments, the nutritional formula includes approximately 0.2 grams of arachidonic acid per L of reconstituted, ready-to-use nutritional formula. In certain embodiments, the nutritional formula includes approximately 0.135 grams of arachidonic acid per L of reconstituted, ready-to-use nutritional formula. In certain embodiments, the nutritional formula includes approximately 0.1 grams of arachidonic acid per L of reconstituted, ready-to-use nutritional formula.

In certain embodiments, the nutritional formula includes linoleic acid. In certain embodiments, the nutritional formula includes approximately 0.25 grams to approximately 7.0 grams of linoleic acid per L of reconstituted, ready-to-use nutritional formula. In certain embodiments, the nutritional formula includes approximately 0.25 grams to approximately 6.0 grams of linoleic acid per L of reconstituted, ready-to-use nutritional formula. In certain embodiments, the nutritional formula includes approximately 5.0 grams to approximately 6.0 grams of linoleic acid per L of reconstituted, ready-to-use nutritional formula. In certain embodiments, the nutritional formula includes approximately 0.25 grams to approximately 5.0 grams of linoleic acid per L of reconstituted, ready-to-use nutritional formula. In certain embodiments, the nutritional formula includes approximately 0.25 grams to approximately 4.0 grams of linoleic acid per L of reconstituted, ready-to-use nutritional formula. In certain embodiments, the nutritional formula includes approximately 0.25 grams to approximately 3.0 grams of linoleic acid per L of reconstituted, ready-to-use nutritional formula. In certain embodiments, the nutritional formula includes approximately 0.25 grams to approximately 2.0 grams of linoleic acid per L of reconstituted, ready-to-use nutritional formula. In certain embodiments, the nutritional formula includes approximately 0.25 grams to approximately 1.0 grams of linoleic acid per L of reconstituted, ready-to-use nutritional formula. In certain embodiments, the nutritional formula includes approximately 0.25 grams to approximately 0.75 grams of linoleic acid per L of reconstituted, ready-to-use nutritional formula. In certain embodiments, the nutritional formula includes approximately 0.25 grams to approximately 0.5 grams of linoleic acid per L of reconstituted, ready-to-use nutritional formula. In certain embodiments, the nutritional formula includes approximately 0.45 grams to approximately 0.5 grams of linoleic acid per L of reconstituted, ready-to-use nutritional formula. In certain embodiments, the nutritional formula includes approximately 5.5 grams to approximately 6.0 grams of linoleic acid per L of reconstituted, ready-to-use nutritional formula. In certain embodiments, the nutritional formula includes approximately 6.0 grams of linoleic acid per L of reconstituted, ready-to-use nutritional formula. In certain embodiments, the nutritional formula includes approximately 5.91 grams of linoleic acid per L of reconstituted, ready-to-use nutritional formula. In certain embodiments, the nutritional formula includes approximately 5.0 grams of linoleic acid per L of reconstituted, ready-to-use nutritional formula. In certain embodiments, the nutritional formula includes approximately 0.47 grams of linoleic acid per L of reconstituted, ready-to-use nutritional formula. In certain embodiments, the nutritional formula includes approximately 0.45 grams of linoleic acid per L of reconstituted, ready-to-use nutritional formula. In certain embodiments, the nutritional formula includes alpha-linolenic acid. In certain embodiments, the nutritional formula includes approximately 0.020 grams to approximately 0.75 grams of alpha-linolenic acid per L of reconstituted, ready-to-use nutritional formula. In certain embodiments, the nutritional formula includes approximately 0.020 grams to approximately 0.50 grams of alpha-linolenic acid per L of reconstituted, ready-to-use nutritional formula. In certain embodiments, the nutritional formula includes approximately 0.020 grams to approximately 0.25 grams of alpha-linolenic acid per L of reconstituted, ready-to-use nutritional formula. In certain embodiments, the nutritional formula includes approximately 0.025 grams to approximately 0.1 grams of alpha-linolenic acid per L of reconstituted, ready-to-use nutritional formula. In certain embodiments, the nutritional formula includes approximately 0.025 grams to approximately 0.075 grams of alpha-linolenic acid per L of reconstituted, ready-to-use nutritional formula. In certain embodiments, the nutritional formula includes approximately 0.05 grams to approximately 0.06 grams of alpha-linolenic acid per L of reconstituted, ready-to-use nutritional formula. In certain embodiments, the nutritional formula includes approximately 0.5 grams to approximately 0.75 grams of alpha-linolenic acid per L of reconstituted, ready-to-use nutritional formula. In certain embodiments, the nutritional formula includes approximately 0.6 grams of alpha-linolenic acid per L of reconstituted, ready-to-use nutritional formula.

In certain embodiments, the nutritional formula includes approximately 0.542 grams of alpha-linolenic acid per L of reconstituted, ready-to-use nutritional formula. In certain embodiments, the nutritional formula includes approximately 0.5 grams of alpha-linolenic acid per L of reconstituted, ready-to-use nutritional formula. In certain embodiments, the nutritional formula includes approximately 0.051 grams of alpha-linolenic acid per L of reconstituted, ready-to-use nutritional formula. In certain embodiments, the nutritional formula includes approximately 0.05 grams of alpha-linolenic acid per L of reconstituted, ready-to-use nutritional formula.

In certain embodiments, the nutritional formula includes prebiotics. In certain embodiments, the prebiotics include galactooligosaccharides, polydextrose, inulin, human milk oligosaccharides, or combinations thereof. In certain embodiments, the prebiotics include galactooligosaccharides, polydextrose, inulin, fructooligosaccharides, human milk oligosaccharides, or combinations thereof. In certain embodiments, the prebiotics include two selected from the group consisting of galactooligosaccharides, polydextrose, and inulin. In certain embodiments, the prebiotics include three selected from the group consisting of galactooligosaccharides, polydextrose, and fructooligosaccharides. In certain embodiments, the prebiotics include galactooligosaccharides and polydextrose. In certain embodiments, the prebiotics include galactooligosaccharides, polydextrose and fructoligosaccharides. In certain embodiments, the galactooligosaccharides are sourced from FrieslandCampina DOMO or DOMO. In certain embodiments, the nutritional formula includes approximately 0.1 grams to approximately 1.0 grams of galactooligosaccharides per L of reconstituted, ready-to-use nutritional formula. In certain embodiments, the nutritional formula includes approximately 0.1 grams to approximately 0.5 grams of galactooligosaccharides per L of reconstituted, ready-to-use nutritional formula. In certain embodiments, the nutritional formula includes approximately 0.3 grams to approximately 1.0 grams of galactooligosaccharides per L of reconstituted, ready-to-use nutritional formula. In certain embodiments, the nutritional formula includes approximately 0.4 grams to approximately 1.0 grams of galactooligosaccharides per L of reconstituted, ready-to-use nutritional formula. In certain embodiments, the nutritional formula includes approximately 0.5 grams to approximately 1.0 grams of galactooligosaccharides per L of reconstituted, ready-to-use nutritional formula. In certain embodiments, the nutritional formula includes approximately 0.75 grams to approximately 0.8 grams of galactooligosaccharides per L of reconstituted, ready-to-use nutritional formula. In certain embodiments, the nutritional formula includes approximately 0.8 grams of galactooligosaccharides per L of reconstituted, ready-to-use nutritional formula. In certain embodiments, the nutritional formula includes approximately 0.4 grams of galactooligosaccharides per L of reconstituted, ready-to-use nutritional formula. In certain embodiments, the nutritional formula includes approximately 0.205 grams of galactooligosaccharides per L of reconstituted, ready-to-use nutritional formula. In certain embodiments, the nutritional formula includes approximately 0.05 grams to approximately 0.1 grams of polydextrose per L of reconstituted, ready-to-use nutritional formula. In certain embodiments, the nutritional formula includes approximately 0.1 grams to approximately 1.5 grams of polydextrose per L of reconstituted, ready-to-use nutritional formula. In certain embodiments, the nutritional formula includes approximately 0.1 grams to approximately 0.5 grams of polydextrose per L of reconstituted, ready-to-use nutritional formula. In certain embodiments, the nutritional formula includes approximately 0.4 grams to approximately 1.0 grams of polydextrose per L of reconstituted, ready-to-use nutritional formula. In certain embodiments, the nutritional formula includes approximately 0.4 grams of polydextrose per L of reconstituted, ready-to-use nutritional formula. In certain embodiments, the nutritional formula includes approximately 0.39 grams of polydextrose per L of reconstituted, ready-to-use nutritional formula. In certain embodiments, the nutritional formula includes approximately 0.3 grams of polydextrose per L of reconstituted, ready-to-use nutritional formula. In certain embodiments, the nutritional formula includes approximately 0.209 grams of polydextrose per L of reconstituted, ready-to-use nutritional formula. In certain embodiments, the nutritional formula includes approximately 0.2 grams of polydextrose per L of reconstituted, ready-to-use nutritional formula. In certain embodiments, the nutritional formula includes approximately 0.06 grams to approximately 0.085 grams of polydextrose per L of reconstituted, ready-to-use nutritional formula. In certain embodiments, the nutritional formula includes approximately 0.08 grams of polydextrose per L of reconstituted, ready-to-use nutritional formula. In certain embodiments, the nutritional formula includes approximately 0.1 grams to approximately 1.0 grams of fructooligosaccharides per L of reconstituted, ready-to-use nutritional formula. In certain embodiments, the nutritional formula includes approximately 0.5 grams to approximately 1.0 grams of fructooligosaccharides per L of reconstituted, ready-to-use nutritional formula. In certain embodiments, the nutritional formula includes approximately 0.1 grams to approximately 0.5 grams of fructooligosaccharides per L of reconstituted, ready-to-use nutritional formula. In certain embodiments, the nutritional formula includes approximately 0.6 grams of fructooligosaccharides per L of reconstituted, ready-to-use nutritional formula. In certain embodiments, the nutritional formula includes approximately 0.583 grams of fructooligosaccharides per L of reconstituted, ready-to-use nutritional formula. In certain embodiments, the nutritional formula includes approximately 0.5 grams of fructooligosaccharides per L of reconstituted, ready-to-use nutritional formula. In certain embodiments, the nutritional formula includes approximately 0.4 grams of fructooligosaccharides per L of reconstituted, ready-to-use nutritional formula. In certain embodiments, the nutritional formula includes approximately 0.364 grams of fructooligosaccharides per L of reconstituted, ready-to-use nutritional formula. In certain embodiments, the nutritional formula includes approximately 0.3 grams of fructooligosaccharides per L of reconstituted, ready-to-use nutritional formula.

In certain embodiments, the prebiotics include galactooligosaccharides and inulin. In certain embodiments, the prebiotics include galactooligosaccharides and fructooligosaccharides. In certain embodiments, the prebiotics include polydextrose and inulin. In certain embodiments, the prebiotics include polydextrose and fructooligosaccharides. In certain embodiments, the prebiotics include galactooligosaccharides and polydextrose. In certain embodiments, the prebiotics include polydextrose, galactooligosaccharides, and fructooligosaccharides. In certain embodiments, the nutritional formula includes approximately 0.1 grams to approximately 1.0 grams of prebiotics per L of reconstituted, ready-to-use nutritional formula. In certain embodiments, the nutritional formula includes approximately 0.4 grams to approximately 1.0 grams of prebiotics per L of reconstituted, ready-to-use nutritional formula. In certain embodiments, the nutritional formula includes approximately 0.4 grams to approximately 0.8 grams of prebiotics per L of reconstituted, ready-to-use nutritional formula. In certain embodiments, the nutritional formula includes approximately 0.8 grams to approximately 1.0 grams of prebiotics per L of reconstituted, ready-to-use nutritional formula. In certain embodiments, the nutritional formula includes approximately 0.906 grams of prebiotics per L of reconstituted, ready-to-use nutritional formula. In certain embodiments, the nutritional formula includes approximately 0.441 grams of prebiotics per L of reconstituted, ready-to-use nutritional formula. In certain embodiments, the prebiotics optionally include one oligosaccharide selected from the group of human milk oligosaccharides consisting of sialyllacto-N-tetraose, lactodifucotetraose, 3'-sialyllactose, 6'-sialyllactose, 3-fucosyllactose, 2'-fucosyllactose, lacto-N-(neo)tetraose, and lacto-N-fucopentaose. In certain embodiments, the nutritional formula includes sialyllacto-N-tetraose. In certain embodiments, the nutritional formula includes lactodifucotetraose. In certain embodiments, the nutritional formula includes 3'-sialyllactose. In certain embodiments, the nutritional formula includes 6'-sialyllactose. In certain embodiments, the nutritional formula includes 3-fucosyllactose. In certain embodiments, the nutritional formula includes 2'-fucosyllactose. In certain embodiments, the nutritional formula includes lacto-N-(neo)tetraose. In certain embodiments, the nutritional formula includes lacto-N-fucopentaose.

In certain embodiments, the nutritional formula further includes vitamins, minerals, nucleotides, or combinations thereof. In certain embodiments, the nutritional formula further includes vitamins. In certain embodiments, the vitamins include Vitamin C, Vitamin E, inositol, Vitamin A, niacin, Vitamin D3, pantothenic acid, Vitamin K1, Vitamin B1, Vitamin B2, Vitamin B6, folic acid, biotin, Vitamin B12, or combinations thereof. In certain embodiments, the vitamins include vitamin C, Vitamin E, inositol, Vitamin A, niacin, Vitamin D3, pantothenic acid, Vitamin K1, Vitamin B1, Vitamin B2, Vitamin B6, folic acid, biotin, and Vitamin B12. In certain embodiments, the nutritional formula further includes minerals. In certain embodiments, the minerals include calcium phosphate, calcium carbonate, potassium chloride, sodium citrate, magnesium phosphate, sodium selenite, iron (II) sulfate, zinc sulfate monohydrate, copper sulfate, manganese (II) sulfate monohydrate, or combinations thereof. In certain embodiments, the minerals include calcium phosphate, calcium carbonate, potassium chloride, sodium citrate, magnesium phosphate, sodium selenite, iron (II) sulfate, zinc sulfate monohydrate, copper sulfate, and manganese (II) sulfate monohydrate. In certain embodiments, the nutritional formula includes nucleotides. In certain embodiments, the nucleotides include adenosine 5'-monophosphate, cytidine 5'-monophosphate, guanosine 5'-monophosphate, uridine 5'-monophosphate, or combinations thereof. In certain embodiments, the nucleotides include adenosine 5'-monophosphate, cytidine 5'-monophosphate, guanosine 5'-monophosphate, and uridine 5'-monophosphate.

In certain embodiments, the nutritional formula further includes L-choline bitartrate, L-carnitine, beta-carotene, taurine, or combinations thereof. In certain embodiments, the nutritional formula includes L-choline bitartrate. In certain embodiments, the nutritional formula includes L-carnitine. In certain embodiments, the nutritional formula includes beta-carotene. In certain embodiments, the nutritional formula includes taurine. In certain embodiments, the nutritional formula further includes L-choline bitartrate, L-carnitine, beta-carotene, and taurine.

In certain embodiments, the nutritional formula optionally further includes lycopene. In certain embodiments, the nutritional formula further includes optional ingredients, including, but not limited to, colorants, flavors, preservatives, further antioxidants, emulsifying agents, buffers, stabilizers, thickening agents, or combinations thereof.

In certain embodiments, the nutritional formula includes approximately 1.0 grams to approximately 1.5 grams of alpha-lactalbumin enriched whey protein concentrate per L of reconstituted, ready-to-use nutritional formula; approximately 1.0 grams to approximately 1.5 grams of beta-casein enriched milk protein per L of reconstituted, ready-to-use nutritional formula; demineralized whey; approximately 25 grams to approximately 30 grams of mildly hydrolyzed milk protein per L of reconstituted, ready-to-use nutritional formula; approximately 0.1 grams to approximately 0.2 grams of lactoferrin per L of reconstituted, ready-to-use nutritional formula; approximately 35 grams to approximately 38 grams of the oleic acid-palmitic acid-oleic acid triglyceride per L of reconstituted, ready-to-use nutritional formula, wherein the triglyceride is vegetable-derived; approximately 1.5 grams to approximately 2.0 grams of lactose per L of reconstituted, ready-to-use nutritional formula; approximately 0.020 grams to approximately 0.025 grams of lutein per L of reconstituted, ready-to-use nutritional formula; approximately 0.05 grams to approximately 0.1 grams of docosahexanoic acid per L of reconstituted, ready-to-use nutritional formula; approximately 0.5 grams to approximately 1.0 grams of arachidonic acid per L of reconstituted, ready-to-use nutritional formula; approximately 0.3 grams to approximately 0.5 grams linoleic acid per L of reconstituted, ready-to-use nutritional formula; approximately 0.025 grams to approximately 0.06 grams alpha-linolenic acid per L of reconstituted, ready-to-use nutritional formula; approximately 0.75 grams to approximately 0.8 grams of galactooligosaccharides per L of reconstituted, ready-to-use nutritional formula; approximately 0.06 grams to approximately 0.085 grams of polydextrose per L of reconstituted, ready-to-use nutritional formula; approximately 0.6 grams to approximately 0.015 grams of Vitamin C per L of reconstituted, ready-to-use nutritional formula; approximately 0.01 grams to approximately 0.05 grams of Vitamin E per L of reconstituted, ready-to-use nutritional formula; approximately 0.01 grams to approximately 0.05 grams of inositol per L of reconstituted, ready-to-use nutritional formula; approximately 0.005 grams to approximately 0.01 grams of Vitamin A per L of reconstituted, ready-to-use nutritional formula, approximately 0.005 grams to approximately 0.009 grams of niacin per L of reconstituted, ready-to-use nutritional formula; approximately 0.00025 grams to approximately 0.006 grams of Vitamin D3 per L of reconstituted, ready-to-use nutritional formula; approximately 0.001 grams to approximately 0.005 grams of pantothenic acid per L of reconstituted, ready-to-use nutritional formula; approximately 0.0005 grams to approximately 0.0015 grams of Vitamin K1 per L of reconstituted, ready-to-use nutritional formula; approximately 0.0001 grams to approximately 0.0002 grams of Vitamin B1 per L of reconstituted, ready-to-use nutritional formula; approximately 0.0005 grams to approximately 0.0009 grams of Vitamin B2 per L of reconstituted, ready-to-use nutritional formula; approximately 0.0005 grams to approximately 0.0008 grams of Vitamin B6 per L of reconstituted, ready-to-use nutritional formula; approximately 0.0001 grams to approximately 0.0002 grams of folic acid per L of reconstituted, ready-to-use nutritional formula; approximately 0.00003 grams to approximately 0.00004 grams of biotin per L of reconstituted, ready-to-use nutritional formula; and approximately 0.000002 grams to approximately 0.000004 grams of Vitamin B12 per L of reconstituted, ready-to-use nutritional formula; approximately 0.3 grams to approximately 0.7 grams of calcium phosphate per L of reconstituted, ready-to-use nutritional formula; approximately 0.25 grams to approximately 0.5 grams of calcium carbonate per L of reconstituted, ready-to-use nutritional formula; approximately 0.3 grams to approximately 0.5 grams of potassium chloride per L of reconstituted, ready-to-use nutritional formula; approximately 0.05 grams to approximately 0.1 grams of sodium citrate per L of reconstituted, ready-to-use nutritional formula; approximately 0.00003 grams to approximately 0.00005 grams of magnesium phosphate per L of reconstituted, ready-to-use nutritional formula; approximately 0.000025 grams to approximately 0.00005 grams of sodium selenite per L of reconstituted, ready-to-use nutritional formula; approximately 0.02 grams to approximately 0.05 grams of iron (II) sulfate per L of reconstituted, ready-to-use nutritional formula; approximately 0.01 grams to approximately 0.03 grams of zinc sulfate monohydrate per L of reconstituted, ready-to-use nutritional formula; approximately 0.002 grams to approximately 0.004 grams of copper sulfate per L of reconstituted, ready-to-use nutritional formula; and approximately 0.000001 grams to approximately 0.000003 grams of manganese (II) sulfate monohydrate per L of reconstituted, ready-to-use nutritional formula; and approximately 0.005 grams to approximately 0.01 grams of adenosine 5'-monophosphate per L of reconstituted, ready-to-use nutritional formula; approximately 0.01 grams to approximately 0.03 grams of cytidine 5'-monophosphate per L of reconstituted, ready-to-use nutritional formula; approximately 0.001 grams to approximately 0.005 grams of guanosine 5'-monophosphate per L of reconstituted, ready-to-use nutritional formula; and approximately 0.01 grams to approximately 0.03 grams of uridine 5'-monophosphate per L of reconstituted, ready-to-use nutritional formula; approximately 0.3 grams to approximately 0.5 grams of L-choline bitartrate per L of reconstituted, ready-to-use nutritional formula; approximately 0.01 grams to approximately 0.03 grams of L-carnitine per L of reconstituted, ready-to-use nutritional formula; approximately 0.0003 grams to approximately 0.0005 grams of beta-carotene per L of reconstituted, ready-to-use nutritional formula; approximately 0.03 grams to approximately 0.07 grams of taurine per L of reconstituted, ready-to-use nutritional formula; approximately 0.3 grams to approximately 0.5 grams of soya lecithin per L of reconstituted, ready-to-use nutritional formula; and approximately 56.0 grams to approximately 58.0 grams of maltodextrin per L of reconstituted, ready-to-use nutritional formula.

In certain embodiments, the nutritional formula includes approximately 2.0 grams to approximately 3.0 grams of alpha-lactalbumin enriched whey protein concentrate per liter (L) of reconstituted, ready-to-use nutritional formula; demineralized whey; whey protein concentrate; skimmed milk powder; approximately 0.1 grams to approximately 0.2 grams of osteopontin per L of reconstituted, ready-to-use formula; approximately 0.01 grams to approximately 0.2 grams of lactoferrin per L of reconstituted, ready-to-use nutritional formula; approximately 35 grams to approximately 38 grams of the oleic acid-palmitic acid-oleic acid triglyceride per L of reconstituted, ready-to-use nutritional formula, wherein the triglyceride is vegetable-derived; approximately 40 grams to approximately 45 grams of lactose per L of reconstituted, ready-to-use nutritional formula; approximately 0.020 grams to approximately 0.025 grams of lutein per L of reconstituted, ready-to-use nutritional formula; approximately 0.05 grams to approximately 0.3 grams of docosahexanoic acid per L of reconstituted, ready-to-use nutritional formula; approximately 0.4 grams to approximately 1.0 grams of arachidonic acid per L of reconstituted, ready-to-use nutritional formula; approximately 0.3 grams to approximately 0.5 grams linoleic acid per L of reconstituted, ready-to-use nutritional formula; approximately 0.025 grams to approximately 0.06 grams alpha-linolenic acid per L of reconstituted, ready-to-use nutritional formula; approximately 0.35 grams to approximately 0.45 grams of galactooligosaccharides per L of reconstituted, ready-to-use nutritional formula; approximately 0.35 grams to approximately 0.45 grams of polydextrose per L of reconstituted, ready-to-use nutritional formula; approximately 0.55 grams to approximately 0.6 grams of fructooligosaccharides per L of reconstituted, ready-to-use nutritional formula; approximately 0.1 grams to approximately 0.15 grams of Vitamin C per L of reconstituted, ready-to-use nutritional formula; approximately 0.01 grams to approximately 0.05 grams of Vitamin E per L of reconstituted, ready-to-use nutritional formula; approximately 0.01 grams to approximately 0.05 grams of inositol per L of reconstituted, ready-to-use nutritional formula; approximately 0.005 grams to approximately 0.01 grams of Vitamin A per L of reconstituted, ready-to-use nutritional formula, approximately 0.005 grams to approximately 0.009 grams of niacin per L of reconstituted, ready-to-use nutritional formula; approximately 0.00025 grams to approximately 0.006 grams of Vitamin D3 per L of reconstituted, ready-to-use nutritional formula; approximately 0.001 grams to approximately 0.005 grams of pantothenic acid per L of reconstituted, ready-to-use nutritional formula; approximately 0.0005 grams to approximately 0.0015 grams of Vitamin K1 per L of reconstituted, ready-to-use nutritional formula; approximately 0.0001 grams to approximately 0.0015 grams of Vitamin B1 per L of reconstituted, ready-to-use nutritional formula; approximately 0.00003 grams to approximately 0.0009 grams of Vitamin B2 per L of reconstituted, ready-to-use nutritional formula; approximately 0.0005 grams to approximately 0.0008 grams of Vitamin B6 per L of reconstituted, ready-to-use nutritional formula; approximately 0.001 grams to approximately 0.002 grams of folic acid per L of reconstituted, ready-to-use nutritional formula; approximately 0.003 grams to approximately 0.004 grams of biotin per L of reconstituted, ready-to-use nutritional formula; and approximately 0.00015 grams to approximately 0.00025 grams of Vitamin B12 per L of reconstituted, ready-to-use nutritional formula; approximately 0.3 grams to approximately 0.7 grams of dicalcium phosphate per L of reconstituted, ready-to-use nutritional formula; approximately 0.25 grams to approximately 0.5 grams of calcium carbonate per L of reconstituted, ready-to-use nutritional formula; approximately 0.3 grams to approximately 0.5 grams of potassium chloride per L of reconstituted, ready-to-use nutritional formula; approximately 0.00004 grams to approximately 0.00006 grams of potassium iodide per L of reconstituted, ready-to-use nutritional formula; approximately 0.4 grams to approximately 0.6 grams potassium citrate per L of reconstituted, ready-to-use nutritional formula; approximately 0.05 grams to approximately 0.1 grams of sodium citrate per L of reconstituted, ready-to-use nutritional formula; approximately 0.00003 grams to approximately 0.00005 grams of dimagnesium phosphate trihydrate per L of reconstituted, ready-to-use nutritional formula; approximately 0.2 grams to approximately 0.3 grams of magnesium chloride hexahydrate per L of reconstituted, ready-to-use nutritional formula; approximately 0.000025 grams to approximately 0.00005 grams of sodium selenite per L of reconstituted, ready-to-use nutritional formula; approximately 0.02 grams to approximately 0.05 grams of iron (II) sulfate per L of reconstituted, ready-to-use nutritional formula; approximately 0.01 grams to approximately 0.03 grams of zinc sulfate monohydrate per L of reconstituted, ready-to-use nutritional formula; approximately 0.002 grams to approximately 0.004 grams of copper sulfate per L of reconstituted, ready-to-use nutritional formula; and approximately 0.000001 grams to approximately 0.000003 grams of manganese (II) sulfate monohydrate per L of reconstituted, ready-to-use nutritional formula; and approximately 0.005 grams to approximately 0.01 grams of adenosine 5'-monophosphate per L of reconstituted, ready-to-use nutritional formula; approximately 0.01 grams to approximately 0.03 grams of cytidine 5'-monophosphate per L of reconstituted, ready-to-use nutritional formula; approximately 0.001 grams to approximately 0.005 grams of guanosine 5'-monophosphate per L of reconstituted, ready-to-use nutritional formula; and approximately 0.01 grams to approximately 0.03 grams of uridine 5'-monophosphate per L of reconstituted, ready-to-use nutritional formula; approximately 0.3 grams to approximately 0.5 grams of L-choline bitartrate per L of reconstituted, ready-to-use nutritional formula; approximately 0.01 grams to approximately 0.03 grams of L-carnitine per L of reconstituted, ready-to-use nutritional formula; approximately 0.0003 grams to approximately 0.0005 grams of beta-carotene per L of reconstituted, ready-to-use nutritional formula; approximately 0.03 grams to approximately 0.07 grams of taurine per L of reconstituted, ready-to-use nutritional formula; and approximately 0.3 grams to approximately 0.5 grams of soya lecithin per L of reconstituted, ready-to-use nutritional formula.

In certain embodiments, the nutritional formula includes approximately 1.38 grams of alpha-lactalbumin enriched whey protein concentrate per L of reconstituted, ready-to-use nutritional formula; approximately 1.38 grams of beta-casein enriched milk protein per L of reconstituted, ready-to-use nutritional formula; demineralized whey; approximately 28 grams of mildly hydrolyzed milk protein per L of reconstituted, ready-to-use nutritional formula; approximately 0.14 grams of lactoferrin per L of reconstituted, ready-to-use nutritional formula; approximately 0.5 grams of the vegetable-derived oleic acid-palmitic acid-oleic acid triglyceride per L of reconstituted, ready-to-use nutritional formula; approximately 1.7 grams of lactose per L of reconstituted, ready-to-use nutritional formula; approximately 0.020 grams of lutein per L of reconstituted, ready-to-use nutritional formula; approximately 0.083 grams of docosahexanoic acid per L of reconstituted, ready-to-use nutritional formula; approximately 0.86 grams of arachidonic acid per L of reconstituted, ready-to-use nutritional formula; approximately 0.47 grams linoleic acid per L of reconstituted, ready-to-use nutritional formula; approximately 0.05 grams alpha-linolenic acid per L of reconstituted, ready-to-use nutritional formula; approximately 0.08 grams of galactooligosaccharides per L of reconstituted, ready-to-use nutritional formula; approximately 0.08 grams of polydextrose per L of reconstituted, ready-to-use nutritional formula; approximately 0.1 grams of Vitamin C; approximately 0.03 grams of Vitamin E, approximately 0.025 grams of inositol; approximately 0.01 grams of Vitamin A; approximately 0.008 grams of niacin; approximately 0.005 grams of Vitamin D3; approximately 0.004 grams of pantothenic acid; approximately 0.001 grams of Vitamin K1; approximately 0.001 grams of Vitamin B1; approximately 0.0008 grams of Vitamin B2; approximately 0.0006 grams of Vitamin B6; approximately 0.0001 grams of folic acid; approximately 0.00004 grams of biotin; and approximately 0.000002 grams of Vitamin B12; approximately 0.6 grams of calcium phosphate; approximately 0.5 grams of calcium carbonate; approximately 0.4 grams of potassium chloride; approximately 0.06 grams of sodium citrate; approximately 0.00003 grams of magnesium phosphate; approximately 0.000025 grams of sodium selenite; approximately 0.046 grams of iron (II) sulfate; approximately 0.017 grams of zinc sulfate monohydrate; approximately 0.026 grams of copper sulfate; and approximately 0.0000018 grams of manganese (II) sulfate monohydrate; and approximately 0.0086 grams of adenosine 5'-monophosphate; approximately 0.016 grams of cytidine 5'-monophosphate; approximately 0.0037 grams of guanosine 5'-monophosphate; and approximately 0.013 grams of uridine 5'-monophosphate; approximately 0.46 grams of L-choline bitartrate; approximately 0.01 grams of L-carnitine; approximately 0.0004 grams of beta-carotene; approximately 0.05 grams of taurine; approximately 0.4 grams of soya lecithin; and approximately 57.5 grams of maltodextrin. The invention provides for powder forms of the nutritional formula, and reconstituted formulas.

In certain embodiments, the nutritional formula includes approximately 2.72 grams of alpha-lactalbumin enriched whey protein concentrate per L of reconstituted, ready-to-use nutritional formula; whey protein concentrate; demineralized whey; skimmed milk powder; approximately 0.16 grams of osteopontin per L of reconstituted, ready-to-use nutritional formula; approximately 0.064 grams of lactoferrin per L of reconstituted, ready-to-use nutritional formula; approximately 5.0 grams of the vegetable-derived oleic acid-palmitic acid-oleic acid triglyceride per L of reconstituted, ready-to-use nutritional formula; approximately 41.814 grams of lactose per L of reconstituted, ready-to-use nutritional formula; approximately 0.021 grams of lutein per L of reconstituted, ready-to-use nutritional formula; approximately 0.067 grams of docosahexanoic acid per L of reconstituted, ready-to-use nutritional formula; approximately 0.135 grams of arachidonic acid per L of reconstituted, ready-to-use nutritional formula; approximately 5.91 grams linoleic acid per L of reconstituted, ready-to-use nutritional formula; approximately 0.542 grams alpha-linolenic acid per L of reconstituted, ready-to-use nutritional formula; approximately 0.399 grams of galactooligosaccharides per L of reconstituted, ready-to-use nutritional formula; approximately 0.399 grams of polydextrose per L of reconstituted, ready-to-use nutritional formula; approximately 0.58 grams of fructooligosaccharides per L of reconstituted, ready-to-use nutritional formula; approximately 0.1 grams of Vitamin C per L of reconstituted, ready-to-use nutritional formula; approximately 0.03 grams of Vitamin E per L of reconstituted, ready-to-use nutritional formula; approximately 0.025 grams of inositol per L of reconstituted, ready-to-use nutritional formula; approximately 0.01 grams of Vitamin A per L of reconstituted, ready-to-use nutritional formula; approximately 0.008 grams of niacin per L of reconstituted, ready-to-use nutritional formula; approximately 0.005 grams of Vitamin D3 per L of reconstituted, ready-to-use nutritional formula; approximately 0.004 grams of pantothenic acid per L of reconstituted, ready-to-use nutritional formula; approximately 0.001 grams of Vitamin K1 per L of reconstituted, ready-to-use nutritional formula; approximately 0.001 grams of Vitamin B1 per L of reconstituted, ready-to-use nutritional formula; approximately 0.00003 grams of Vitamin B2 per L of reconstituted, ready-to-use nutritional formula; approximately 0.0006 grams of Vitamin B6 per L of reconstituted, ready-to-use nutritional formula; approximately 0.001 grams of folic acid per L of reconstituted, ready-to-use nutritional formula; approximately 0.004 grams of biotin per L of reconstituted, ready-to-use nutritional formula; approximately 0.002 grams of Vitamin B12 per L of reconstituted, ready-to-use nutritional formula; approximately 0.001 grams of folic acid per L of reconstituted, ready-to-use nutritional formula; approximately 0.004 grams of biotin per L of reconstituted, ready-to-use nutritional formula; approximately 0.6 grams of dicalcium phosphate per L of reconstituted, ready-to-use nutritional formula; approximately 0.5 grams of calcium carbonate per L of reconstituted, ready-to-use nutritional formula; approximately 0.4 grams of potassium chloride per L of reconstituted, ready-to-use nutritional formula; approximately 0.00005 grams of potassium iodide per L of reconstituted, ready-to-use nutritional formula; approximately 0.54 grams of potassium citrate per L of reconstituted, ready-to-use nutritional formula; approximately 0.28 grams of magnesium chloride per L of reconstituted, ready-to-use nutritional formula; approximately 0.39 grams of sodium citrate per L of reconstituted, ready-to-use nutritional formula; approximately 0.00003 grams of dimagnesium phosphate per L of reconstituted, ready-to-use nutritional formula; approximately 0.000025 grams of sodium selenite per L of reconstituted, ready-to-use nutritional formula; approximately 0.046 grams of iron (II) sulfate per L of reconstituted, ready-to-use nutritional formula; approximately 0.017 grams of zinc sulfate monohydrate per L of reconstituted, ready-to-use nutritional formula; approximately 0.026 grams of copper sulfate per L of reconstituted, ready-to-use nutritional formula; and approximately 0.0000018 grams of manganese (II) sulfate monohydrate per L of reconstituted, ready-to-use nutritional formula; approximately 0.0086 grams of adenosine 5'-monophosphate per L of reconstituted, ready-to-use nutritional formula; approximately 0.016 grams of cytidine 5'-monophosphate per L of reconstituted, ready-to-use nutritional formula; approximately 0.0037 grams of guanosine 5'-monophosphate per L of reconstituted, ready-to-use nutritional formula; approximately 0.013 grams of uridine 5'-monophosphate per L of reconstituted, ready-to-use nutritional formula; approximately 0.46 grams of L-choline bitartrate per L of reconstituted, ready-to-use nutritional formula; approximately 0.01 grams of L-carnitine per L of reconstituted, ready-to-use nutritional formula; approximately 0.0004 grams of beta-carotene per L of reconstituted, ready-to-use nutritional formula; approximately 0.05 grams of taurine per L of reconstituted, ready-to-use nutritional formula; and approximately 0.4 grams of soya lecithin per L of reconstituted, ready-to-use nutritional formula. The invention provides for powder forms of the nutritional formula, and reconstituted formulas.

In certain embodiments, the present disclosure provides a nutritional formula comprising:
  a) alpha-lactalbumin enriched whey protein concentrate;
  b) beta-casein enriched milk protein;
  c) mildly hydrolyzed milk protein;
  d) lactoferrin;
  e) oleic acid-palmitic acid-oleic acid triglyceride, wherein palmitic acid is at the SN-2 position of the glycerol backbone of the triglyceride;
  f) lactose, wherein the lactose is reduced lactose;
  g) lutein;
  h) docosahexanoic acid;

i) arachidonic acid;
j) galactooligosaccharides; and
k) polydextrose.

In certain embodiments, the present disclosure provides a nutritional formula comprising:
a) alpha-lactalbumin enriched whey protein concentrate;
b) lactoferrin;
c) oleic acid-palmitic acid-oleic acid triglyceride, wherein palmitic acid is at the SN-2 position of the glycerol backbone of the triglyceride;
d) lactose, wherein the lactose is reduced lactose;
e) lutein;
f) docosahexanoic acid;
g) arachidonic acid;
h) galactooligosaccharides;
i) polydextrose; and
j) osteopontin.

In certain embodiments, the present disclosure provides a nutritional formula comprising:
a) alpha-lactalbumin enriched whey protein concentrate;
b) beta-casein enriched milk protein;
c) mildly hydrolyzed milk protein;
d) lactoferrin;
e) oleic acid-palmitic acid-oleic acid triglyceride, wherein palmitic acid is at the SN-2 position of the glycerol backbone of the triglyceride;
f) lactose, wherein the lactose is reduced lactose;
g) lutein;
h) docosahexanoic acid;
i) arachidonic acid;
j) galactooligosaccharides;
k) polydextrose; and
l) inulin.

In certain embodiments, the present disclosure provides a nutritional formula comprising:
a) alpha-lactalbumin enriched whey protein concentrate;
b) lactoferrin;
c) oleic acid-palmitic acid-oleic acid triglyceride, wherein palmitic acid is at the SN-2 position of the glycerol backbone of the triglyceride;
d) lactose, wherein the lactose is reduced lactose;
e) lutein;
f) docosahexanoic acid;
g) arachidonic acid;
h) galactooligosaccharides;
i) polydextrose;
j) osteopontin; and
k) fructooligosaccharides.

In certain embodiments, the present disclosure provides a nutritional formula comprising:
a) alpha-lactalbumin enriched whey protein concentrate;
b) beta-casein enriched milk protein;
c) mildly hydrolyzed milk protein;
d) lactoferrin;
e) oleic acid-palmitic acid-oleic acid triglyceride, wherein palmitic acid is at the SN-2 position of the glycerol backbone of the triglyceride;
f) lactose, wherein the lactose is reduced lactose;
g) lutein;
h) docosahexanoic acid;
i) arachidonic acid;
j) galactooligosaccharides;
k) polydextrose;
l) inulin;
m) vitamins;
n) minerals;
o) nucleotides;
p) soya lecithin;
q) maltodextrin;
r) beta-carotene; and
s) taurine.

In certain embodiments, the present disclosure provides a nutritional formula comprising:
a) alpha-lactalbumin enriched whey protein concentrate;
b) lactoferrin;
c) oleic acid-palmitic acid-oleic acid triglyceride, wherein palmitic acid is at the SN-2 position of the glycerol backbone of the triglyceride;
d) lactose, wherein the lactose is reduced lactose;
e) lutein;
f) docosahexanoic acid;
g) arachidonic acid;
h) galactooligosaccharides;
i) polydextrose;
j) osteopontin;
k) fructooligosaccharides;
l) vitamins;
m) minerals;
n) nucleotides;
o) soya lecithin;
p) maltodextrin;
q) beta-carotene; and
r) taurine.

In certain embodiments, the nutritional formula is provided in a powder form. In certain embodiments, the nutritional formula is provided in a liquid form.

The present disclosure also provides reconstituted formulations comprising a powder form of the nutritional formula described herein, reconstituted with water to yield a ready-to-feed liquid. In certain embodiments, the nutritional formulation is reconstituted with 900 mL water to form approximately 1 L of reconstituted nutritional formulation. In certain embodiments, the nutritional formulation is reconstituted with approximately 1 L water to form approximately 1.1 L of reconstituted nutritional formulation.

Also provided herein are liquid concentrates of a nutritional formula described herein, wherein the liquid concentrates can be diluted to form a ready-to-feed liquid.

Kits and Administration

Nutritional formulas described herein can be prepared by any method known in the art of nutritional formulation and manufacturing. In general, such preparatory methods include combining ingredients of the nutritional formula into an aqueous slurry, including protein, carbohydrate, fat or lipid blends, prebiotics, minerals, lutein, beta-carotene, or combinations thereof, heating the aqueous slurry to approximately 140° F., and then homogenizing, pasteurizing, cooling, and spray drying the aqueous slurry. Other materials, including vitamins, minerals, nucleotides, polyunsaturated fatty acids (e.g., arachidonic acid and docosahexanoic acid), proteins (e.g., lactoferrin), or combinations thereof, may be added to the spray dried solution, followed by further processing and packaging.

In certain embodiments, such preparatory methods for preparing the nutritional formulas include a two-step process. The first step involves the addition of macroingredients, including protein (e.g., alpha-lactalbumin enriched whey protein concentrate, beta-casein enriched milk protein, mildly hydrolyzed milk protein), carbohydrate (e.g., maltodextrin, and lactose), prebiotics (e.g., galactooligosaccharides and polydextrose), base mineral premix, fat or lipid (e.g., lecithin), lutein, beta-carotene, or combinations thereof, into a base mixing tank containing water (e.g., reverse osmosis processed water) and outfitted with a high speed mixer. In certain embodiments, the first step involves the addition of macroingredients, including protein (e.g., alpha-lactalbumin enriched whey protein concentrate, skimmed milk powder, demineralized whey), carbohydrate (e.g., lactose), prebiotics (e.g., galactooligosaccharides, fructrooligosaccharides and polydextrose), base mineral premix, fat or lipid (e.g., lecithin), lutein, beta-carotene, or combinations thereof, into a base mixing tank containing water (e.g., reverse osmosis processed water) and outfitted with a high speed mixer. A vegetable oil blend (e.g., Betapol DP9100, including OPO SN-2 oil) is then added into the base mixing tank and heated (e.g., heated to 140° F.). This forms an aqueous slurry. The aqueous slurry is then purified. In certain embodiments, the aqueous slurry is first transferred into a two-stage homogenizer, followed by transfer to a two-stage pasteurizer. Next, the slurry is dried. In certain embodiments, hot filtered air (e.g., with a temperature of approximately 350° F. to approximately 400° F.) is used to spray dry the mixture. Sifting is used to trap large particles, wherein these larger trapped particles are added back into the tall form spray drier to achieve complete drying. Once a low moisture level (e.g., a moisture level of approximately 2% or less) is achieved, the dried powder is transferred into a powder hopper for bagging into large nitrogen flushed bags (e.g., bags of 20-40 kg).

The second stage of the process generally involves the addition of the vitamin premix, trace minerals premix, and nucleotides premix to one bag of 20-40 kg (e.g., a 25 kg bag), as a base. This mixture is placed in a small mixer with lactoferrin (e.g., freeze-dried lactoferrin), along with polyunsaturated fatty acids (e.g., microencapsulated arachidonic acid and docosahexanoic acid), and then gently blended. A total of approximately thirty to forty (e.g., thirty-five) of each bag (e.g., each 25 kg bag) that has undergone the above additions are combined in a large paddle blender. Next, the powdered forms of the nutritional formula are packaged and distributed. In certain embodiments, a screen magnet, vertical filler, and case sealer are used to fill and seal individual packets of the powder nutritional formula (e.g., powder packets), wherein approximately one hundred (e.g., 96) powder packets can be produced per minute. The completed product is placed into containers for mass distribution.

Also encompassed by the disclosure are kits (e.g., packages of powder nutritional formula). The kits provided may comprise a nutritional formulation described herein and a container (e.g., a suitable container), or reconstituted formulas described herein. Thus, in one aspect, provided are kits including a container comprising a nutritional formulation described herein. In certain embodiments, the kits are useful for providing nutrition (e.g., promoting postnatal development of gastrointestinal functions, nutrient absorption, immune system development, etc.) to a subject in need thereof (e.g., an infant). In certain embodiments, the kits are useful in a method described herein.

In certain embodiments, a kit described herein further includes instructions for using the powder nutritional formula included in the kit. The nutritional formula may be provided in convenient serving for administering (serving) to a subject. The kit may include a dehydrated nutritional formula and a diluting agent (e.g., water). In certain embodiments, the diluting agent is water. The kit may include multiple dosage units. For example, the kit may include 1-100 servings. A kit described herein may also include information as required by a regulatory agency such as the U.S. Food and Drug Administration (FDA). In certain embodiments, the kits include instructions on calculating a serving and/or providing nutrition to a subject in need thereof. Also encompassed by the disclosure are devices (e.g., bottles) for feeding a subject with the nutritional formula or reconstituted formula.

Methods of Administration and Feeding

The present disclosure provides methods of providing nutrition to (e.g., feeding) a subject (e.g., newborn, infant) in need thereof. In certain embodiments, the method of providing nutrition to a subject comprises administering (e.g., feeding) a nutrition formula described herein to a subject. In certain embodiments, the administered nutrition formula is a previously reconstituted, ready-to-feed liquid. In certain embodiments, the method of providing nutrition to a subject comprises reconstituting the nutrition formula in powder form with water to form a ready-to-feed liquid. In certain embodiments, the methods of the disclosure include feeding the subject with the reconstituted formula. In certain embodiments, the method of providing nutrition (e.g., feeding) may be useful for providing nutrition as well as postnatal development of gastrointestinal functions, promoting nutrient absorption, immune system development, and combinations thereof. In certain embodiments, the methods of providing nutrition may be useful for postnatal development of gastrointestinal functions. In certain embodiments, the methods of providing nutrition may be useful for promoting nutrient absorption. In certain embodiments, the methods of providing nutrition may be useful for immune system development.

In certain embodiments, the methods of the disclosure include administering to a subject in need thereof an effective amount of a nutrition formula described herein. In certain embodiments, the subject in need thereof is a human. In certain embodiments, the subject in need thereof is a child. In certain embodiments, the subject in need thereof is an infant. In certain embodiments, the subject in need thereof is a newborn. In certain embodiments, the subject in need thereof is a toddler. In certain embodiments, the subject in need thereof is an adult. In certain embodiments, the subject in need thereof is an adolescent.

EXAMPLES

In order that the present disclosure may be more fully understood, the following examples are set forth. The examples described in this application are offered to illustrate the nutritional formulas, reconstituted formulas, and methods provided herein and are not to be construed in any way as limiting their scope.

Preparation of the Formulations Described Herein

The nutritional formulas provided herein can be prepared from readily available starting materials using the following exemplary methods and procedures. For example, nutritional formulas can be prepared according to Example 1.

Example 1. Exemplary Preparation of Nutritional Formula

This example illustrates a nutritional formula disclosed herein, including a method for making the formula. The formula ingredients are listed in the following table.

| Ingredient | Quantity g/L reconstituted formula** |
|---|---|
| S1 Base: | |
| Maltodextrin | 57.463 |
| Vegetable blend (contains OPO) | 36.519 |
| Milk protein hydrolysate | 27.983 |
| Carrier (lactose) | 1.082 |
| Dicalcium phosphate (anhydrous) | 0.607 |
| Calcium carbonate (precipitated) | 0.500 |
| L-Choline bitartrate (conditioned) | 0.462 |
| Potassium chloride | 0.445 |
| Magnesium chloride 6 H$_2$O | 0.281 |
| Trisodium citrate 2 H$_2$O | 0.059 |
| L-carnitine | 0.0110300 |
| Potassium Iodide | 0.0000541 |
| Potassium citrate | 0.0000345 |
| Dimagnesium phosphate 3 H$_2$O | 0.0000345 |
| Sodium selenite anhydrous | 0.0000257 |
| Lactose | 1.656 |
| α-lactalbumin enriched Whey Protein Concentrate | 1.385 |
| β-casein enriched milk protein | 1.385 |
| Galactoligosaccharides | 0.800 |
| Polydextrose | 0.080 |
| Soya lecithin | 0.414061 |
| Lutein | 0.020635 |
| β-carotene | 0.000407 |
| Dry blend Vitamin premix: | |
| Vitamin C (ascorbic acid) | 0.1096875 |
| Carrier (lactose) | 0.087075 |
| Taurine | 0.0513 |
| Vitamin E 50% (dl-α-tocopheryl acetate, 500 IU) | 0.0324 |
| Inositol | 0.02565 |
| Vitamin A (retinol palmitate), 250000 IU | 0.00972 |
| Niacin (Niacinamide) | 0.0081 |
| Vitamin D3 (cholecalciferol), 100000 IU | 0.0054 |
| Pantothenic acid (calcium-D-pantothenate) | 0.003915 |
| Vitamin K1, 5% | 0.00135 |
| Vitamin B1 (thiamine hydrochloride) | 0.00105975 |
| Vitamin B2 (riboflavin) | 0.000837 |
| Vitamin B6 (pyridoxine hydrochloride) | 0.000594 |
| Folic acid | 0.0001215 |
| Biotin | 0.00003915 |
| Vitamin B12 (cyanocobalamin) | 0.000002025 |
| Dry blend trace mineral premix: | |
| Carrier (lactose) | 0.06885 |
| Iron (II) sulphate (dried) | 0.046845 |
| Zinc sulphate 1H$_2$O | 0.016605 |
| Copper sulphate | 0.002646 |
| Manganese (II) sulphate 1H$_2$O | 0.0000018 |
| Dry blend, nucleotides premix | |
| Cytidine 5'-Monophosphate free acid | 0.016416 |
| Uridine 5'-Monophosphate Disodium Salt | 0.012798 |
| Guanosine 5'-Monophosphate Disodium Salt | 0.003672 |
| Adenosine 5'-Monophosphate free acid | 0.00864 |
| Carrier | 0.012474 |
| *Crypthecodinium Cohnii* Oil powder | 0.432 |
| *Mortierella alpina* Oil powder | 0.864 |
| Lactoferrin | 0.135 |

**900 mL of water added to ingredients to give 1 Liter (L) reconstituted formula The nutritional formula is typically prepared using a two-step process. The first step involves the addition of macroingredients (e.g., alpha-lactalbumin enriched whey protein concentrate, beta-casein enriched milk protein, mildly hydrolyzed milk protein, maltodextrin, and lactose), prebiotics (e.g., galactooligosaccharides and polydextrose), base mineral premix, lecithin, lutein, and beta-carotene into a base mixing tank containing reverse osmosis processed water and outfitted with a high speed mixer. The vegetable oil blend (e.g., Betapol DP9100, including OPO SN-2 oil) is then added into the base mixing tank and heated to 140° F.

This example illustrates a nutritional formula disclosed herein, including a method for making the formula. The formula ingredients are listed in the following table.

| Ingredient | Quantity g/L reconstituted formula** |
|---|---|
| S1 Base: | |
| Demineralized whey | 24.436 |
| Whey protein concentrate | 5.702 |
| Vegetable blend (contains OPO) | 36.519 |
| Skimmed milk powder | 16.780 |
| Carrier (lactose) | 1.082 |
| Dicalcium phosphate (anhydrous) | 0.607 |
| Calcium carbonate (precipitated) | 0.500 |
| L-Choline bitartrate (conditioned) | 0.462 |
| Potassium chloride | 0.445 |
| Magnesium chloride 6•H$_2$O | 0.281 |
| Sodium citrate | 0.397 |
| L-carnitine | 0.0110300 |
| Potassium iodide | 0.0000541 |
| Potassium citrate | 0.543 |
| Dimagnesium phosphate 3•H$_2$O | 0.0000345 |
| Sodium selenite anhydrous | 0.0000257 |
| Lactose | 40.582 |
| α-lactalbumin enriched Whey Protein Concentrate | 2.715 |
| β-casein enriched milk protein | 1.385 |
| Galactoligosaccharides | 0.399 |
| Polydextrose | 0.399 |
| Fructooligosaccharides | 0.583 |
| Soya lecithin | 0.414061 |
| Lutein | 0.020635 |
| β-carotene | 0.000407 |
| Osteopontin | 0.163 |
| Dry blend Vitamin premix: | |
| Vitamin C (ascorbic acid) | 0.1096875 |
| Carrier (lactose) | 0.08114 |
| Taurine | 0.0513 |
| Vitamin E 50% (dl-α-tocopheryl acetate, 500 IU) | 0.0324 |
| Inositol | 0.02565 |
| Vitamin A (retinol palmitate), 250000 IU | 0.00972 |
| Niacin (Niacinamide) | 0.0081 |
| Vitamin D3 (cholecalciferol), 100000 IU | 0.0054 |
| Pantothenic acid (calcium-D-pantothenate) | 0.003915 |
| Vitamin K1, 5% | 0.00135 |
| Vitamin B1 (thiamine hydrochloride) | 0.00105975 |
| Vitamin B2 (riboflavin) | 0.00003375 |
| Vitamin B6 (pyridoxine hydrochloride) | 0.000594 |
| Folic acid | 0.001215 |
| Biotin | 0.003915 |
| Vitamin B12 (cyanocobalamin) | 0.002025 |
| Dry blend trace mineral premix: | |
| Carrier (lactose) | 0.06885 |
| Iron (II) sulphate (dried) | 0.046845 |
| Zinc sulphate 1•H$_2$O | 0.016605 |
| Copper sulphate | 0.002646 |
| Manganese (II) sulphate 1•H$_2$O | 0.0000018 |
| Dry blend, nucleotides premix | |
| Cytidine 5'-Monophosphate free acid | 0.016416 |
| Uridine 5'-Monophosphate Disodium Salt | 0.012798 |
| Guanosine 5'-Monophosphate Disodium Salt | 0.003672 |
| Adenosine 5'-Monophosphate free acid | 0.00864 |
| Carrier | 0.084024 |
| *Crypthecodinium Cohnii* Oil powder | 0.432 |
| *Mortierella alpina* Oil powder | 0.864 |
| Lactoferrin | 0.064 |

**900 mL of water added to ingredients to give 1 Liter (L) reconstituted formula The nutritional formula is typically prepared using a two-step process. The first step involves the addition of macroingredients (e.g., alpha-lactalbumin enriched whey protein concentrate, skimmed milk powder, and lactose), prebiotics (e.g., galactooligosaccharides, fructooligosaccharides, and polydextrose), base mineral premix, lecithin, lutein, and beta-carotene into a base mixing tank containing reverse osmosis processed water and outfitted with a high speed mixer. The vegetable oil blend (e.g., Betapol DP9100, including OPO SN-2 oil) is then added into the base mixing tank and heated to 140° F.

The slurry is then transferred into a two-stage homogenizer, followed by transfer to a two-stage pasteurizer. Hot filtered air with a temperature of approximately 350° F. to approximately 400° F. is used to spray dry the mixture. Sifting is used to trap large particles, wherein these larger particles are added back into the tall form spray drier to achieve complete drying. When a moisture level of approximately 2% or less is achieved, powder is transferred into a powder hopper for bagging into 25 kg nitrogen flushed bags.

The second stage of the process used to prepare nutritional formula involves the addition of the vitamin premix, trace minerals premix, and nucleotides premix to one 25 kg bag base. This mixture is placed in a small mixer with freeze-dried lactoferrin, along with microencapsulated arachidonic acid/docosahexaenoic acid, both which require gentle blending in a dry environment. The addition of microencapsulated DHA/ARA and lactoferrin at this stage in the process aids in the preservation of intact ingredients and prevents oxidative degradation during processing, blending, poaching, and storage. A total of 35 of each 25 kg bag base powder packets that have undergone the above additions are combined in a large paddle blender. A screen magnet, vertical filler, and case sealer are used to fill and seal individual packets of the powder nutritional formula, wherein approximately 96 powder packets can be produced per minute. The completed product is placed into suitable containers for distribution.

The prepared nutritional formulation is analyzed to obtain the following nutrional information.

| Items | /per 100 g powder | /per 100 ml prepared formula | /per 100 kcal |
| --- | --- | --- | --- |
| Energy, kJ | 2155 | 291 | 418 |
| Energy, kcal | 515 | 70 | 100 |
| Protein, g | 11.3 | 1.5 | 2.2 |
| Fat, g | 27.8 | 3.8 | 5.4 |
| OPO, g | 3.6 | 0.5 | 0.7 |
| Carbohydrate, g | 55 | 7.4 | 10.7 |
| Lactose, g | 55 | 7.4 | 10.7 |
| Dietary fibre, mg | 757 | 102 | 147 |
| Galactoligosaccharides, mg | 152 | 20.5 | 29.5 |
| Polydextrose, mg | 155 | 20.9 | 30 |
| Fructooligosaccharides, mg | 364 | 49.2 | 70.7 |
| Linoleic acid, mg | 4378 | 591 | 850 |
| α-Linolenic acid, mg | 402 | 54.2 | 78 |
| DHA, mg | 50 | 6.7 | 9.7 |
| ARA, mg | 100 | 13.5 | 19.4 |
| Vitamin A, IU | 1545 | 209 | 300 |
| Vitamin D, IU | 309 | 42 | 60 |
| Vitamin E, IU | 10.3 | 1.4 | 2 |
| Vitamin K, mcg | 46.4 | 6.3 | 9 |
| Thiamine (Vitmain B1), mcg | 412 | 56 | 80 |
| Riboflavin (Vitamin B2), mcg | 721 | 97 | 140 |
| Vitamin B6, mcg | 309 | 42 | 60 |
| Vitmain B12, mcg | 1.5 | 0.2 | 0.3 |
| Niacin, mcg | 5150 | 695 | 1000 |
| Folic acid (Folacin), mcg | 82 | 11 | 16 |
| Pantothenic acid, mcg | 3090 | 417 | 600 |
| Biotin, mcg | 15.5 | 2.1 | 3 |
| Vitamin C (Ascorbic acid), mg | 62 | 8.3 | 12 |
| Choline, mg | 124 | 17 | 24 |
| Inositol, mg | 31 | 4.2 | 6 |
| Nucleotides, mg | 20 | 2.7 | 3.9 |
| L-Carnitine, mg | 7 | 0.9 | 1.4 |
| Lutein, mcg | 93 | 12.5 | 18 |
| β-carotene, mcg | 100 | 14 | 19 |
| Taurine, mg | 30 | 4.1 | 5.8 |
| Lactoferrin, mg | 40 | 5.4 | 7.8 |
| Osteopontin, mg | 93 | 12.5 | 18 |
| Calcium, mg | 402 | 54 | 78 |
| Phosphorus, mg | 221 | 30 | 43 |
| Magnesium, mg | 41 | 6 | 8 |
| Iron, mg | 9.3 | 1.3 | 1.8 |
| Zinc, mg | 5.2 | 0.7 | 1 |
| Manganese, mcg | 77 | 10 | 15 |
| Copper, mcg | 386 | 52 | 75 |
| Iodine, mcg | 52 | 7 | 10 |
| Selenium, mcg | 14.4 | 1.9 | 2.8 |
| Sodium, mg | 139 | 19 | 27 |
| Potassium, mg | 556 | 75 | 108 |
| Chloride, mg | 324 | 44 | 63 |

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A reconstituted, ready-to-use nutritional formula comprising:
   a) alpha-lactalbumin enriched whey protein concentrate comprising at least 30% alpha-lactalbumin by weight of the alpha-lactalbumin enriched whey protein concentrate; wherein the reconstituted, ready-to-use nutritional formula comprises 0.25 grams to 5.0 grams of alpha-lactalbumin enriched whey protein concentrate per L of the reconstituted, ready-to-use nutritional formula;
   b) 0.01 grams to 1.0 grams of lactoferrin per L of the reconstituted, ready-to-use nutritional formula;
   c) 0.5 grams to 5.0 grams of oleic acid-palmitic acid-oleic acid triglyceride (OPO triglyceride) per L of the reconstituted, ready-to-use nutritional formula, wherein palmitic acid is at the SN-2 position of the glycerol backbone of the OPO triglyceride;
   d) lactose;
   e) lutein;
   f) 0.01 grams to 0.1 grams of docosahexanoic acid per L of the reconstituted, ready-to-use nutritional formula;
   g) 0.01 grams to 1.0 grams of arachidonic acid per L of the reconstituted, ready-to-use nutritional formula;
   h) galactooligosaccharides, wherein the reconstituted, ready-to-use nutritional formula comprises 0.1 grams to 0.5 grams of galactooligosaccharides per L of the reconstituted, ready-to-use nutritional formula;
   i) polydextrose, wherein the reconstituted, ready-to-use nutritional formula comprises 0.1 grams to 0.5 grams of polydextrose per L of the reconstituted, ready-to-use nutritional formula;
   j) fructooligosaccharides, wherein the reconstituted, ready-to-use nutritional formula comprises 0.1 grams to 0.6 grams of fructooligosaccharides per L of the reconstituted, ready-to-use nutritional formula;
   wherein the reconstituted, ready-to-use nutritional formula comprises 0.1 grams to 1.0 grams per L of a combination of galactooligosaccharides, polydextrose, and fructooligosaccharides; and
   k) 0.01 grams to 0.25 grams of osteopontin per L of the reconstituted, ready-to-use nutritional formula.

2. The reconstituted, ready-to-use nutritional formula of claim 1 further comprising linoleic acid.

3. The reconstituted, ready-to-use nutritional formula of claim 1 further comprising alpha-linolenic acid.

4. The reconstituted, ready-to-use nutritional formula of claim 1 further comprising nucleotides.

5. The reconstituted, ready-to-use nutritional formula of claim 4, wherein the nucleotides comprise adenosine 5'-monophosphate, cytidine 5'-monophosphate, guanosine 5'-monophosphate, uridine 5'-monophosphate, or a combination thereof.

6. The reconstituted, ready-to-use nutritional formula of claim 1 further comprising beta-carotene.

7. The reconstituted, ready-to-use nutritional formula of claim 1, wherein the reconstituted, ready-to-use nutritional formula comprises 0.5 grams to 3.0 grams of alpha-lactalbumin enriched whey protein concentrate per L of the reconstituted, ready-to-use nutritional formula.

8. The reconstituted, ready-to-use nutritional formula of claim 1, wherein the reconstituted, ready-to-use nutritional formula comprises 0.05 grams to 0.2 grams of lactoferrin per L of the reconstituted, ready-to-use nutritional formula.

9. The reconstituted, ready-to-use nutritional formula of claim 1, wherein the reconstituted, ready-to-use nutritional formula comprises 3.0 grams to 5.0 grams of the OPO triglyceride per L of the reconstituted, ready-to-use nutritional formula.

10. The reconstituted, ready-to-use nutritional formula of claim 1, wherein the reconstituted, ready-to-use nutritional formula comprises 0.0025 grams to 0.05 grams of lutein per L of the reconstituted, ready-to-use nutritional formula.

11. The reconstituted, ready-to-use nutritional formula of claim 1, wherein the reconstituted, ready-to-use nutritional formula comprises 0.2 grams to 0.4 grams of polydextrose per L of the reconstituted, ready-to-use nutritional formula.

12. The reconstituted, ready-to-use nutritional formula of claim 1, wherein the reconstituted, ready-to-use nutritional formula comprises 0.8 grams to 1.0 grams of prebiotics per L of the reconstituted, ready-to-use nutritional formula, wherein the prebiotics comprise galactooligosaccharides, fructooligosaccharides, and polydextrose.

13. The reconstituted, ready-to-use nutritional formula of claim 1, wherein the docosahexanoic acid, arachidonic acid, or a combination thereof are microencapsulated.

14. The reconstituted, ready-to-use nutritional formula of claim 1 further comprising one or more human milk oligosaccharides selected from the group consisting of sialyl-lacto-N-tetraose, lactodifucotetraose, 3'-sialyllactose, 6'-sialyllactose, 3-fucosyllactose, 2'-fucosyllactose, lacto-N-(neo)tetraose, and lacto-N-fucopentaose.

15. The reconstituted, ready-to-use nutritional formula of claim 1, wherein the reconstituted, ready-to-use nutritional formula comprises 0.1 grams to 0.2 grams of osteopontin per L of the reconstituted, ready-to-use nutritional formula.

16. The reconstituted, ready-to-use nutritional formula of claim 1, wherein the reconstituted, ready-to-use nutritional formula comprises 0.4 grams to 0.6 grams of fructooligosaccharides per L of the reconstituted, ready-to-use nutritional formula.

17. The reconstituted, ready-to-use nutritional formula of claim 1, wherein the reconstituted, ready-to-use nutritional formula comprises 0.1 grams to 0.15 grams of osteopontin per L of the reconstituted, ready-to-use nutritional formula.

18. The reconstituted, ready-to-use nutritional formula of claim 1, wherein the reconstituted, ready-to-use nutritional formula comprises 0.25 grams to 3.0 grams of alpha-lactalbumin per L of the reconstituted, ready-to-use nutritional formula.

19. The reconstituted, ready-to-use nutritional formula of claim 1 further comprising vitamins, minerals, or a combination thereof.

20. The reconstituted, ready-to-use nutritional formula of claim 1 further comprising taurine.

21. A dehydrated powder form of a nutritional formula, wherein the dehydrated powder form of the nutritional formula comprises:
 a) 0.19 grams to 3.7 grams of an alpha-lactalbumin enriched whey protein concentrate per 100 grams of the dehydrated powder form of the nutritional formula, wherein the alpha-lactalbumin enriched whey protein concentrate comprises at least 30% alpha-lactalbumin by weight of the alpha-lactalbumin enriched whey protein concentrate;
 b) lactoferrin, wherein the dehydrated powder form of the nutritional formula comprises 3.7 0.007 grams to 0.74 grams of lactoferrin per 100 grams of the dehydrated powder form of the nutritional formula;
 c) 0.37 grams to 3.7 grams of oleic acid-palmitic acid-oleic acid triglyceride (OPO triglyceride) per 100 grams of the dehydrated powder form of the nutritional formula, wherein palmitic acid is at the SN-2 position of the glycerol backbone of the OPO triglyceride;
 d) lactose;
 e) lutein;
 f) docosahexanoic acid, wherein the dehydrated powder form of the nutritional formula comprises 0.007 grams to 0.074 grams of docosahexanoic acid per 100 grams of the dehydrated powder form of the nutritional formula;
 g) 0.0074 grams to 0.74 grams of arachidonic acid per 100 grams of the dehydrated powder form of the nutritional formula;
 h) galactooligosaccharides, wherein the dehydrated powder form of the nutritional formula comprises 0.074 grams to 0.37 grams of galactooligosaccharides per 100 grams of the dehydrated powder form of the nutritional formula;
 i) polydextrose, wherein the dehydrated powder form of the nutritional formula comprises 0.074 grams to 0.37 grams of polydextrose per 100 grams of the dehydrated powder form of the nutritional formula;
 j) fructooligosaccharides, wherein the dehydrated powder form of the nutritional formula comprises 0.074 grams to 0.44 grams of fructooligosaccharides per 100 grams of the dehydrated powder form of the nutritional formula;
 wherein the dehydrated powder form of the nutritional formula comprises 0.074 grams to 0.74 grams of a combination of galactooligosaccharides, polydextrose, and fructooligosaccharides; and
 k) 0.007 grams to 0.19 grams of osteopontin per 100 grams of the dehydrated powder form of the nutritional formula.

22. A method of providing nutrition to a subject, wherein the method comprises administering the reconstituted, ready-to-use nutritional formula of claim 1 to the subject.

23. A method of providing nutrition to a subject, wherein the method comprises: feeding the subject the reconstituted, ready-to-use nutritional formula of claim 1.

24. A method of providing nutrition to a subject, wherein the method comprises: reconstituting the dehydrated powder form of the formula of claim 21 with water to form a ready-to-feed liquid.

25. A kit comprising:
 i. one or more packages of the dehydrated powder form of the nutritional formula of claim 21, and
 ii. instructions for feeding the dehydrated powder form of the nutritional formula to a subject.

* * * * *

UNITED STATES PATENT AND TRADEMARK OFFICE
CERTIFICATE OF CORRECTION

| | |
|---|---|
| PATENT NO. | : 11,547,744 B2 |
| APPLICATION NO. | : 16/315132 |
| DATED | : January 10, 2023 |
| INVENTOR(S) | : James McGrath et al. |

It is certified that error appears in the above-identified patent and that said Letters Patent is hereby corrected as shown below:

In the Claims

In Claim 5, at Column 46, Lines 7-9:
"5 '-monophosphate, cytidine 5'-monophosphate, guanosine 5 '-monophosphate, uridine 5'-monophosphate, or a combination thereof."
Is replaced with:
--5'-monophosphate, cytidine 5'-monophosphate, guanosine 5'-monophosphate, uridine 5'-monophosphate, or a combination thereof.--.

In Claim 21, at Column 47, Lines 17-18:
"nutritional formula comprises 3.7 0.007 grams to 0.74 grams"
Is replaced with:
--nutritional formula comprises 0.007 grams to 0.74 grams--.

Signed and Sealed this
Twenty-eighth Day of February, 2023

Katherine Kelly Vidal
*Director of the United States Patent and Trademark Office*